(12) United States Patent
Higashikawa et al.

(10) Patent No.: US 11,464,405 B2
(45) Date of Patent: Oct. 11, 2022

(54) VISUAL FUNCTION TEST DEVICE, VISUAL FUNCTION TRAINING DEVICE, AND METHOD THEREOF

(71) Applicant: nac Image Technology Inc., Tokyo (JP)

(72) Inventors: Takuji Higashikawa, Tokyo (JP); Norihito Numa, Tokyo (JP); Shogo Nakamura, Tokyo (JP)

(73) Assignee: NAC IMAGE TECHNOLOGY INC., Tokyo (JP)

( * ) Notice: Subject to any disclaimer, the term of this patent is extended or adjusted under 35 U.S.C. 154(b) by 515 days.

(21) Appl. No.: 16/620,136

(22) PCT Filed: Jun. 8, 2018

(86) PCT No.: PCT/JP2018/022115
§ 371 (c)(1),
(2) Date: Dec. 6, 2019

(87) PCT Pub. No.: WO2018/225867
PCT Pub. Date: Dec. 13, 2018

(65) Prior Publication Data
US 2020/0100668 A1    Apr. 2, 2020

(30) Foreign Application Priority Data

Jun. 8, 2017  (JP) .............................. JP2017-113743

(51) Int. Cl.
*A61B 3/032* (2006.01)
*G06T 7/70* (2017.01)
(Continued)

(52) U.S. Cl.
CPC ............ *A61B 3/032* (2013.01); *A61B 3/0008* (2013.01); *A61B 3/0041* (2013.01);
(Continued)

(58) Field of Classification Search
CPC ..... A61B 3/032; A61B 3/0008; A61B 3/0041; A61B 3/08; A61B 3/0091; A61B 3/113;
(Continued)

(56) References Cited

U.S. PATENT DOCUMENTS

2013/0044290 A1* 2/2013 Kawamura .............. A61B 3/08
351/239

FOREIGN PATENT DOCUMENTS

| JP | 2007-209384 A | 8/2007 |
| JP | 2011-161122 A | 8/2011 |
| JP | 2011-206105 A | 10/2011 |

OTHER PUBLICATIONS

International Search Report ("ISR") of PCT/JP2018/022115 dated Sep. 4, 2018.
Written Opinion ("WO") of PCT/JP2018/022115 dated Sep. 4, 2018.

* cited by examiner

*Primary Examiner* — Mohammed A Hasan
(74) *Attorney, Agent, or Firm* — Metrolex IP Law Group, PLLC

(57) ABSTRACT

The visual function test device of an embodiment comprises a test subject display device and an operator display device. A target display portion displays a target image to be viewed by the test subject onto the test subject display device. A visual axis estimation portion estimates a visual axis of the test subject when the target image is viewed. A position display portion displays a display position of the test target image and a viewpoint position that corresponds to the estimated visual axis, onto the operator display device, and thus a tester can objectively recognize a gazing state of the test subject and surely perform the test, which enhances the reliability of the test.

20 Claims, 24 Drawing Sheets

(51) Int. Cl.
*A61B 3/00* (2006.01)
*G06T 7/00* (2017.01)

(52) U.S. Cl.
CPC .............. *G06T 7/0012* (2013.01); *G06T 7/70* (2017.01); *G06T 2207/10048* (2013.01); *G06T 2207/30041* (2013.01)

(58) Field of Classification Search
CPC ........... A61B 3/02; G06T 7/0012; G06T 7/70; G06T 2207/10048; G06T 2207/30041; A61H 2205/024; A61H 5/00
USPC ........................................................ 351/221
See application file for complete search history.

VISUAL FUNCTION TEST DEVICE, VISUAL FUNCTION TRAINING DEVICE, AND METHOD THEREOF

TECHNICAL FIELD

Embodiments of the present invention relate to a visual function test device, a visual function training device, and a method thereof.

BACKGROUND

Test devices for testing various visual functions are conventionally known.

For example, visual function tests may include a visual acuity test (a test with a single eye opened and a test with both eyes opened), a simultaneous perception test, a fusion test, a stereopsis test (a near vision test and a far vision test), a nine gaze directions test (Hess chart test), a visual field test, a preferential looking method test, an aniseikonia test, etc.

PRIOR ART DOCUMENT

Patent Document

Patent document 1: Japanese Patent Number JP 4,824,420B

SUMMARY OF THE INVENTION

Problems to be Solved by the Invention

In any of the tests, however, a subjective response of a test subject is indispensable, and it has been difficult for an examiner to recognize which position the test subject is actually using as a gaze position in the test.

Therefore, there has been a possibility that the test is performed while the test subject does not gaze at the gaze position as instructed by the examiner, and thus the reliability of the test may not be ensured.

Especially when an infant or the like is to be tested, it has been difficult for the examiner to reliably recognize whether or not the infant follows the examiner's instruction.

Also in a visual function training device for training a visual function, a subjective response of the trainee is indispensable. Therefore, there have been similar issues, for example, it is not possible for the trainee to recognize which position the trainee actually uses as a gaze position in the training, and thus an effective guidance cannot be always provided.

In view of the issues described above, the object of the present invention is to provide a visual function test device, in which the examiner can objectively recognize a gaze state of the test subject and surely perform a test or training, a visual function training device that can improve the reliability of the test, and a method thereof.

Means to Solve the Problems

A visual function test device of an embodiment comprises a test subject display device and an operator display device.

A target display portion displays a target image to be viewed by the test subject, onto the test subject display device.

A visual axis estimation portion estimates a visual axis of the test subject when the target image is viewed by the test subject.

Accordingly, a position display portion displays a display position of the target image and a viewpoint position that corresponds to the estimated visual axis, onto the operator display device.

In addition, a display portion displays an eyeball image of the test subject onto the operator display device.

A visual function training device of an embodiment comprises a trainee display device and an operator display device.

A target display portion displays a target image to be viewed by the trainee, onto the trainee display device.

A visual axis estimation portion estimates a visual axis of the trainee when the target image is viewed by the trainee.

Accordingly, a position display portion displays a display position of the target image and a viewpoint position that corresponds to the estimated visual axis, onto the operator display device.

A display portion displays an eyeball image of the trainee onto the operator display device.

EMBODIMENTS FOR IMPLEMENTING THE INVENTION

Preferred embodiments are described referring to drawings.

[1] First Embodiment

Figure 1:
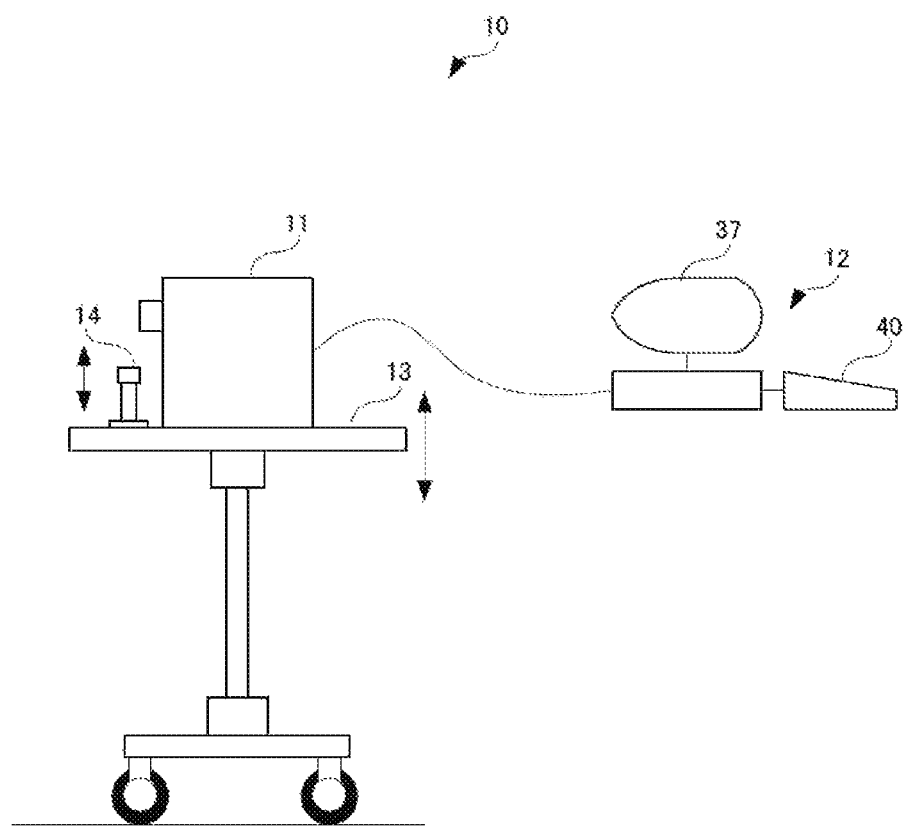
FIG. 1 is a schematic configuration block diagram of a visual function test device of an embodiment.

FIG. 1 is a schematic configuration block diagram of a visual function test device of an embodiment.

A visual function test device 10 may generally comprise a test unit 11 for testing a test subject, and an operator unit 12 used by an operator who performs various operations for performing a test.

The test unit 11 is disposed on a height-adjustable test table 13. A height-adjustable jaw table 14, on which the test subject's jaw is to be placed, is provided on the test table 13, thereby the position of the eye of the test subject can be adjusted to an optimum position relative to the test unit 11, in cooperation with the test table 13.

The operator unit 12 is generally configured as a personal computer.

Figure 2:
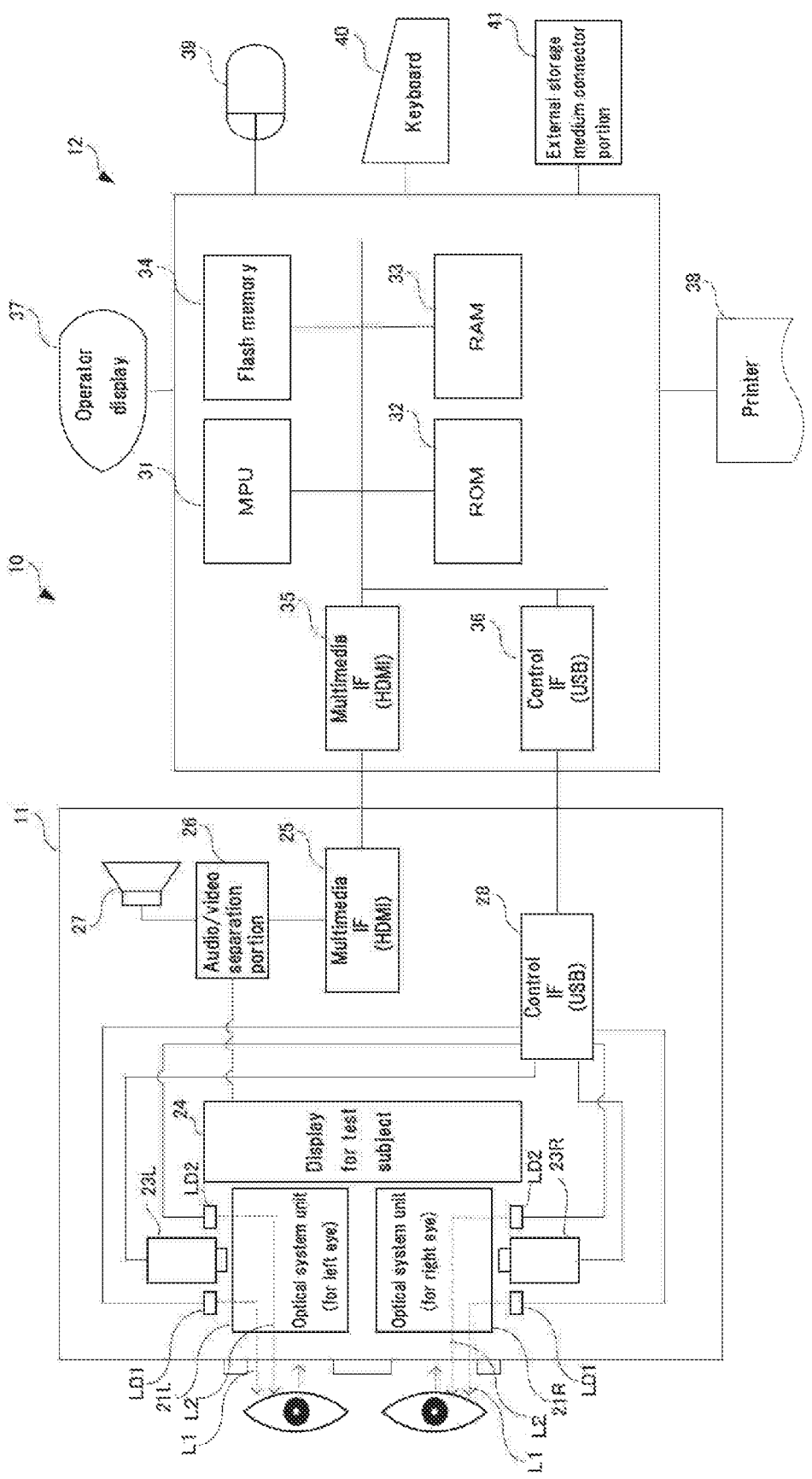
FIG. 2 is a detailed configuration block diagram of a visual function test device according to a first embodiment.

FIG. 2 is a detailed configuration block diagram of a visual function test device according to a first embodiment.

The test unit 11 comprises: optical system units 21R and 21L capable of adjusting a viewing angle, a test distance, or the like, and for guiding infrared light (IR) test light L1 and L2 (hereinafter referred to as test light L when they are not necessary to be distinguished from each other) to respective predetermined positions to be illuminated, and each of the optical system units 21R and 21L corresponding to the left eye or right eye; a pair of IR lighting devices LD1 and LD2 for illuminating the eye of the test subject using the test light L through an optical system unit 21; and a pair of eyeball cameras (imaging cameras) 23R and 23L for imaging mainly an eyeball of the test subject.

The test unit 11 further comprises: a test subject display 24 for displaying various images for the test subject; a multimedia interface (IF) 25, such as HDMI (Registered trademark), for performing an interface operation of audio data and video (image) data; an audio/video separation portion 26 for performing audio/video separation of an output signal of the multimedia interface 25; a loudspeaker portion 27 for performing audio output; and a control interface (IF) 28, such as a USB, to which a control signal is input.

The operator unit 12 comprises: an MPU 31 for controlling the operator unit 12; a ROM 32 for storing control data including an operating system (OS) in a nonvolatile manner; a RAM 33 for temporarily storing various data and also used as a working area of the MPU 31; a flash memory 34 for storing various data in a nonvolatile and updatable manner; and a multimedia interface (IF) 35, such as HDMI, for performing an interface operation of audio data and video (image) data.

The operator unit 12 further comprises: a control interface (IF) 36 for performing various interface operations for control; an operator display 37 connected through the multimedia interface 35 and providing various information to an operator; a printer 38 for printing various data; a mouse 39 functioning as a pointing device and performing various operations; a keyboard 40 for performing various operations and inputting various data; and an external storage medium connector portion 41 for connecting an external storage medium, such as a USB memory, an IC card (for example, SD card (Registered trademark)), or the like, to read the data of the test subject or record the test result data.

A flow of a test in the visual function test device 10 according to an embodiment is briefly described.

In the description below, a case in which the visual function test device is configured as a nine gaze directions test device is described as an example.

Figure 3:
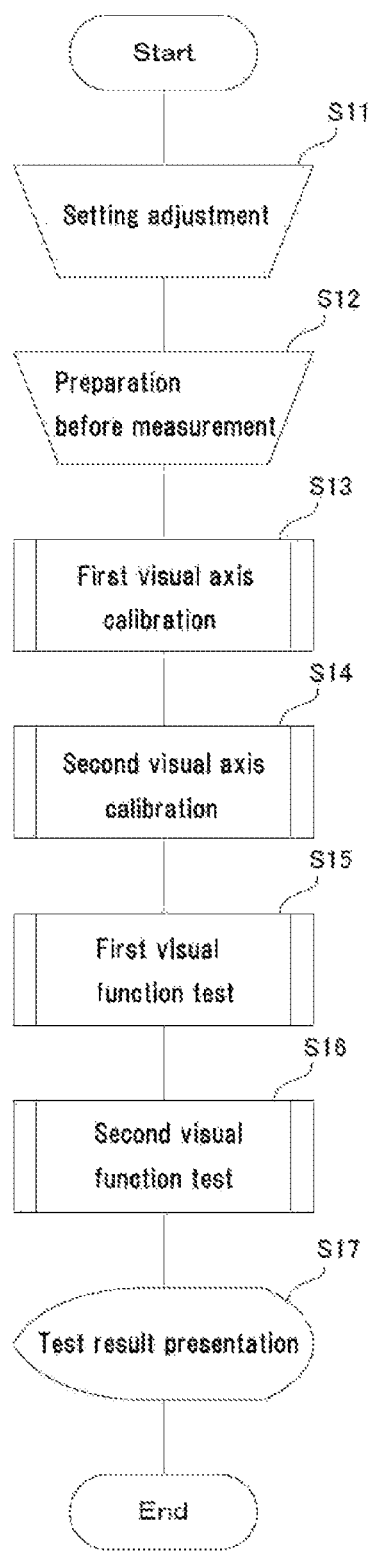
FIG. 3 is a schematic diagram illustrating a test procedure in a visual function test device.

FIG. 3 is a schematic diagram illustrating a test procedure in a visual function test device.

When a test is to be performed in the visual function test device 10, the procedure described below is generally performed.

Initially, the operator adjusts equipment settings for a test subject so that the test subject can be in a comfortable posture during the test (Step S11).

Next, a preparation before measurement for the test subject is performed (Step S12).

Subsequently, a first visual axis calibration for determining a visual axis of one of the eyes (e.g. right eye) is performed (Step S13).

Then, a second visual axis calibration for determining the visual axis of the other eye (e.g. left eye) is performed (Step S14).

Subsequently, a first visual function test is performed as a visual function test (nine gaze directions test in the present embodiment) of one of the eyes (e.g. right eye) (Step S15).

Then, a second visual function test is performed, which is a visual function test of the other eye (e.g. left eye) (Step S16).

Test result is presented on the operator display, or printed (Step S17).

Each processing is described in detail below.

{1} Setting Adjustment

Initially, the operator roughly adjusts the height of the jaw table 14 and the test table 13 so that the patient, who is the test subject, can take an ease posture during the test (Step S11).

{2} Preparation Before Measurement

Then, the operator operates the mouse 39 or the keyboard 40 to instruct a preparation before measurement.

This causes the MPU 31 of the operator unit 12 to display a preparation before measurement image on the test subject display 24 of the test unit 11, through the multimedia interface 35 and the multimedia interface 25, and perform the preparation before measurement in order to optimize the position of the test subject's face for the test (Step S12).

The preparation before measurement is described in detail below.

Figure 4:
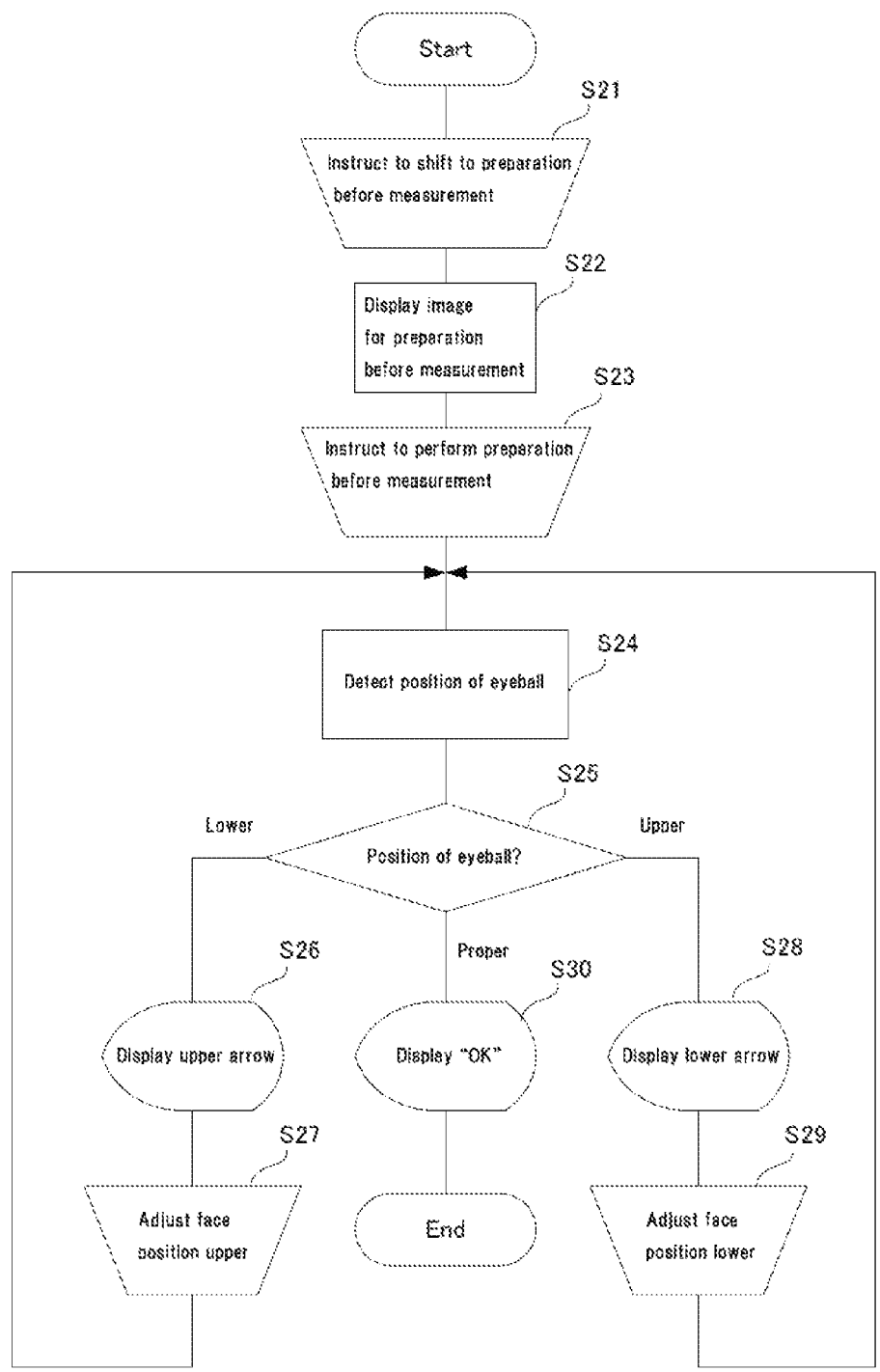
FIG. 4 is a processing flowchart of a preparation before measurement.

FIG. 4 is a processing flowchart of a preparation before measurement.

Figure 5:
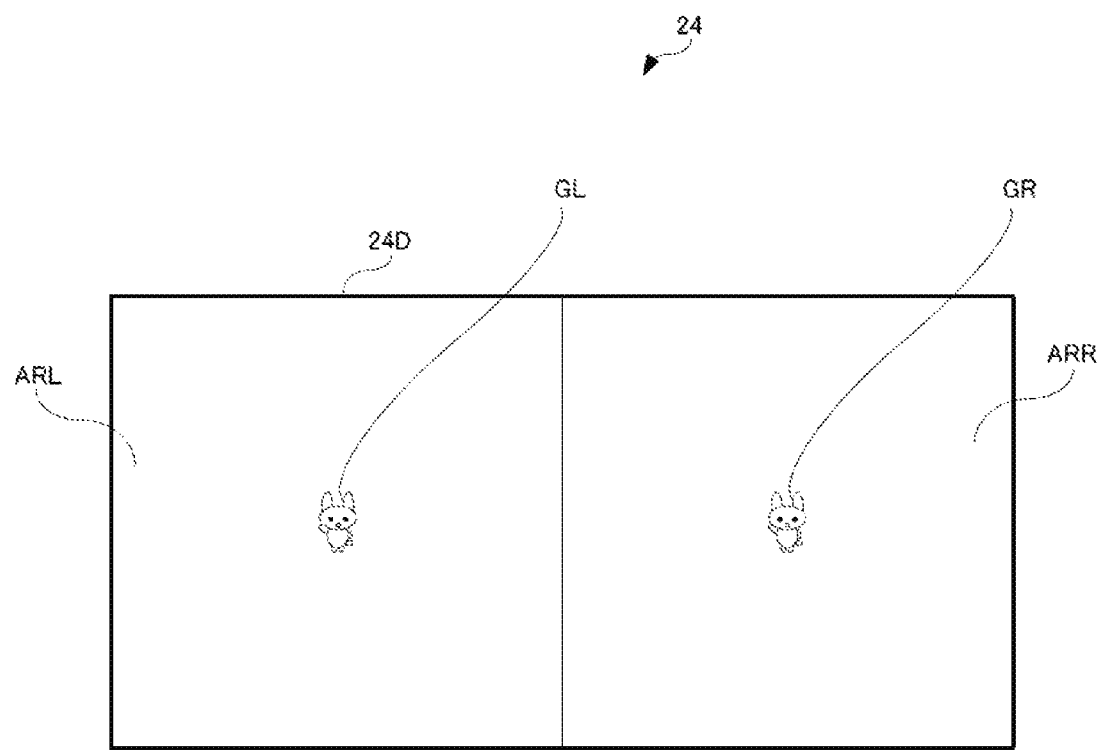
FIG. 5 is a diagram illustrating a preparation before measurement.

FIG. 5 is a diagram illustrating the preparation before measurement.

When the operator operates the mouse 39 to instruct to shift to the preparation before measurement (Step S21), preparation before measurement images GL and GR for the left and right eyes are displayed on a display screen 24D of the test subject display 24 of the test unit 11 (Step S22).

More specifically, as illustrated in FIG. 5, the preparation before measurement image GL for the left eye is displayed at a center portion of a left eye image display area ARL of the display screen 24D of the test subject display 24. Similarly, the preparation before measurement image GR for the right eye is displayed at a center portion of a right eye image display area ARR of the display screen 24D of the test subject display.

In this case, the left eye image display area ARL is visible only from the left eye of the test subject through the optical system unit 21L. Similarly, the right eye image display area ARR is visible only from the right eye of the test subject through the optical system unit 21R.

Then, the operator directs the test subject to gaze at the respective preparation before measurement images GL and GR through the optical system units 21L and 21R, and operates the mouse 39 or the keyboard 40 to instruct the operator unit 12 to perform the preparation before measurement (Step S23).

Figure 6:
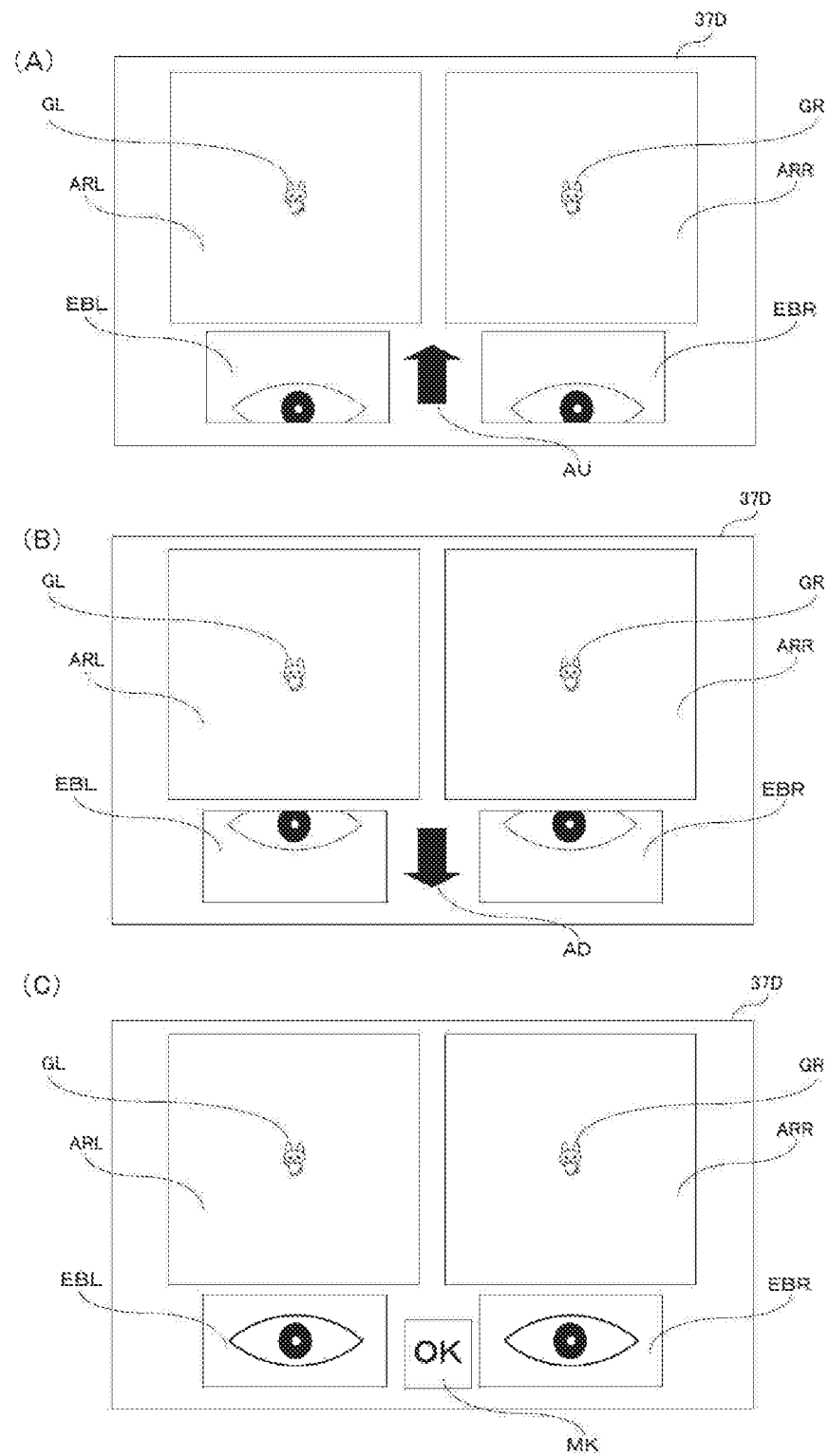
FIG. 6 is a diagram illustrating display examples of an operator display at the time of the preparation before measurement.

FIG. 6 is a diagram illustrating a display example of an operator display at the time of the preparation before measurement.

As a result, the MPU 31 of the operator unit 12 displays the display content of the test subject display 24 onto the operator display 37. In addition, the MPU 31 displays an image of the left eye of the test subject, which is taken by a left eyeball camera 23L, in a left eyeball display area EBL. Similarly, the MPU 31 displays an image of the right eye of the test subject, which is taken by a right eyeball camera 23R, in a right eyeball display area EBR.

Positions of the eyeballs are detected based on the image taken by the eyeball camera 23L and the image taken by the right eyeball camera 23R (Step S24).

This enables the MPU 31 of the operator unit 12 to determine whether or not the position of the center of the pupil in a vertical direction is located at a position appropriate with respect to the optical axes of the cameras 23R, 23L (the position at which the optical axis of the camera 23R, 23L passes through substantially the center of the pupil) (Step S25).

In the determination in Step S25, if the center of the pupil is located lower than the center position that corresponds to the optical axis of the eyeball camera 23L, 23R ("Lower" in Step S25), then the eyeball image of the left eye of the test subject is displayed in the left eyeball display area EBL of the display screen 37D of the operator display 37, as illustrated in FIG. 6A, through the control by the MPU 31. On the other hand, the eyeball image of the right eye of the test subject is displayed in the right eyeball display area EBR. In addition, an upward adjustment instruction mark AU is displayed in an area between the left eyeball display area EBL and the right eyeball display area EBR, instructing to adjust the height of the jaw table 14 in a direction to increase the height of the jaw table 14 (Step S26).

Accordingly, the operator adjusts the height of the jaw table 14 in the direction to increase its height (Step S27).

It is also possible to adjust the height of the test table 13, if adjustment cannot be made only by adjusting the height of the jaw table 14. In this case, the optical axes of the cameras 23R and 23L are located upper than the center of the pupil, and thus the height of the test table 13 is to be adjusted downward.

Then, the MPU 31 of the operator unit 12 returns the processing again to Step S24, and repeats the procedure described above.

In determination in Step S25, if the pupil center is located upper than the center position that corresponds to the optical axis of the eyeball camera 23L, 23R ("Above" in step S25), then a downward adjustment instruction mark AD is displayed as illustrated in FIG. 6B, instructing to adjust the height of the jaw table 14 downward (Step S28).

Accordingly, the operator adjusts the height of the jaw table 14 downward (Step S29).

It is also possible to adjust the height of the test table 13, if adjustment cannot be made only by adjusting the height of the jaw table 14. In this case, the optical axes of the cameras 23R and 23L are located lower than the pupil center, and thus the height of the test table 13 is adjusted to be heightened.

Then, the MPU 31 of the operator unit 12 returns the processing again to Step S24, and repeats the procedure described above.

In the determination of Step S25, if the pupil center is located near the center position that corresponds to the optical axes of the eyeball cameras 23L, 23R ("Proper" in Step S25), then an image indicating that the preparation before measurement is completed, which is an "OK" mark MK in the case in FIG. 6C, is displayed on the operator display 37 (Step S30). The operator thus may proceed to an actual test procedure.

{3} First Visual Axis Calibration

In the description below, it is assumed that a visual axis calibration of the right eye is performed as a first visual axis calibration.

Figure 7:
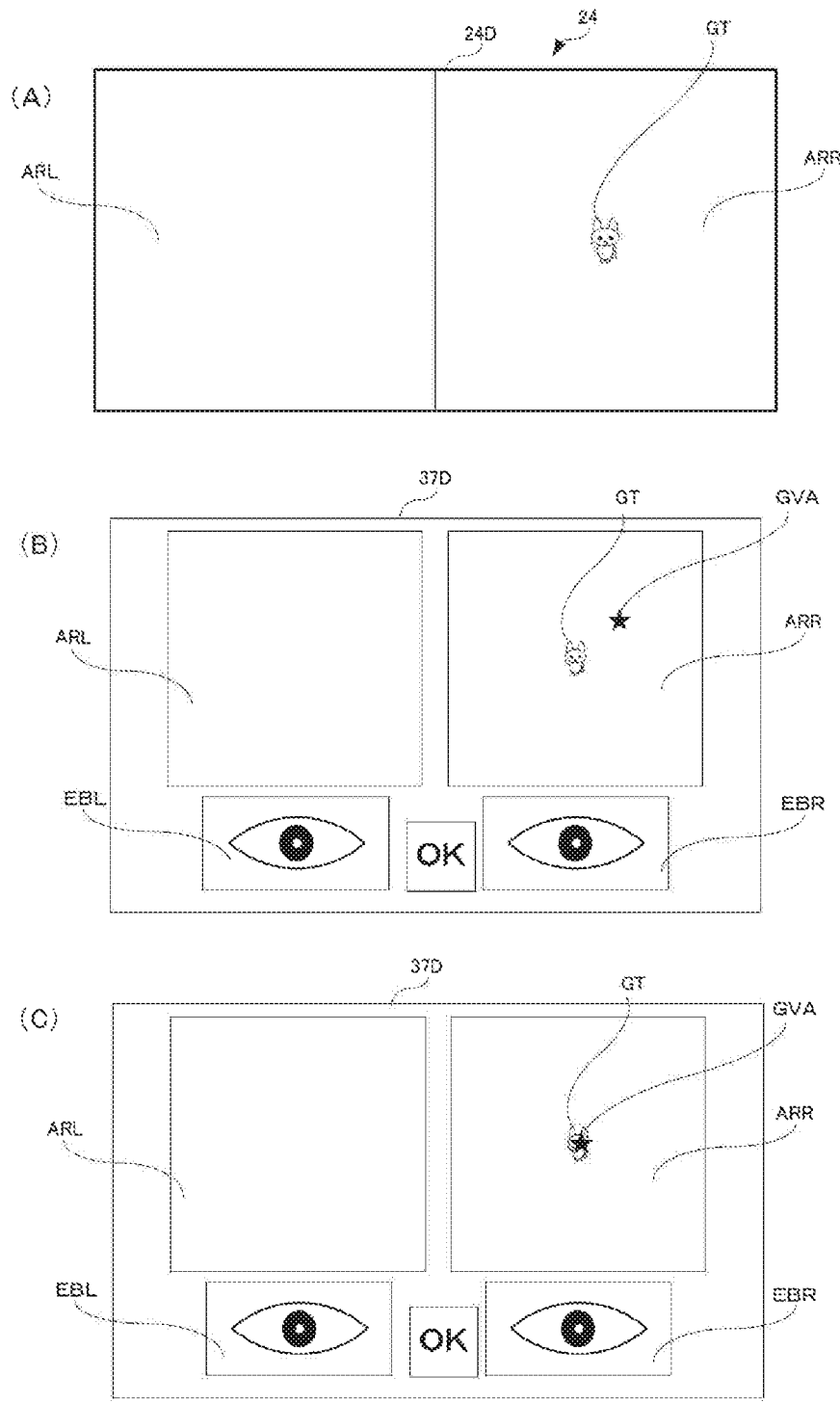
FIG. 7 is a diagram illustrating a visual axis calibration of the right eye.

FIG. 7 is a diagram illustrating a visual axis calibration of the right eye.

Figure 8:
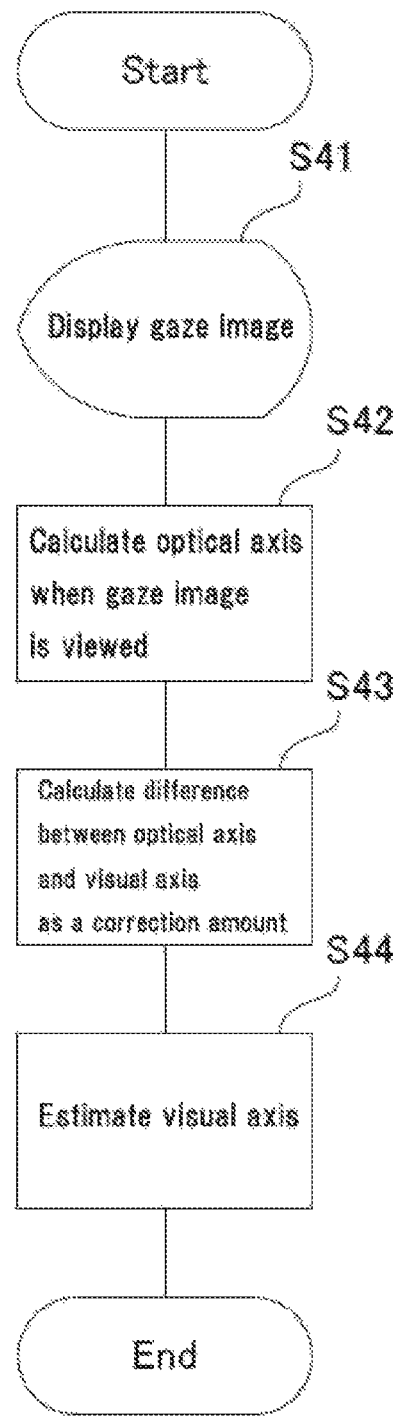
FIG. 8 is a processing flowchart of a visual axis estimation processing.

FIG. 8 is a processing flowchart of a visual axis estimation processing of an embodiment.

When the operator instructs the calibration of the visual axis of the right eye through an operation of a keyboard or a mouse, the MPU 31 of the operator unit 12 displays a gaze image GT, which is to be gazed at by the test subject using the right eye, in the right eye image display area of the display screen of the test subject display through the multimedia interface 35, as illustrated in FIG. 7A (Step S41).

At this time, the operator prompts the test subject to gaze at the gaze image GT in order to restrict changes in the position of the visual axis (line of vision) of the test subject.

Accordingly, the MPU 31 of the operator unit 12 calculates the optical axis of the right eye in a state where the changes in the visual axis of the right eye are restricted (Step S42).

A method of an optical axis calculation according to the first embodiment is described in detail, with reference to the drawings.

Figure 9:
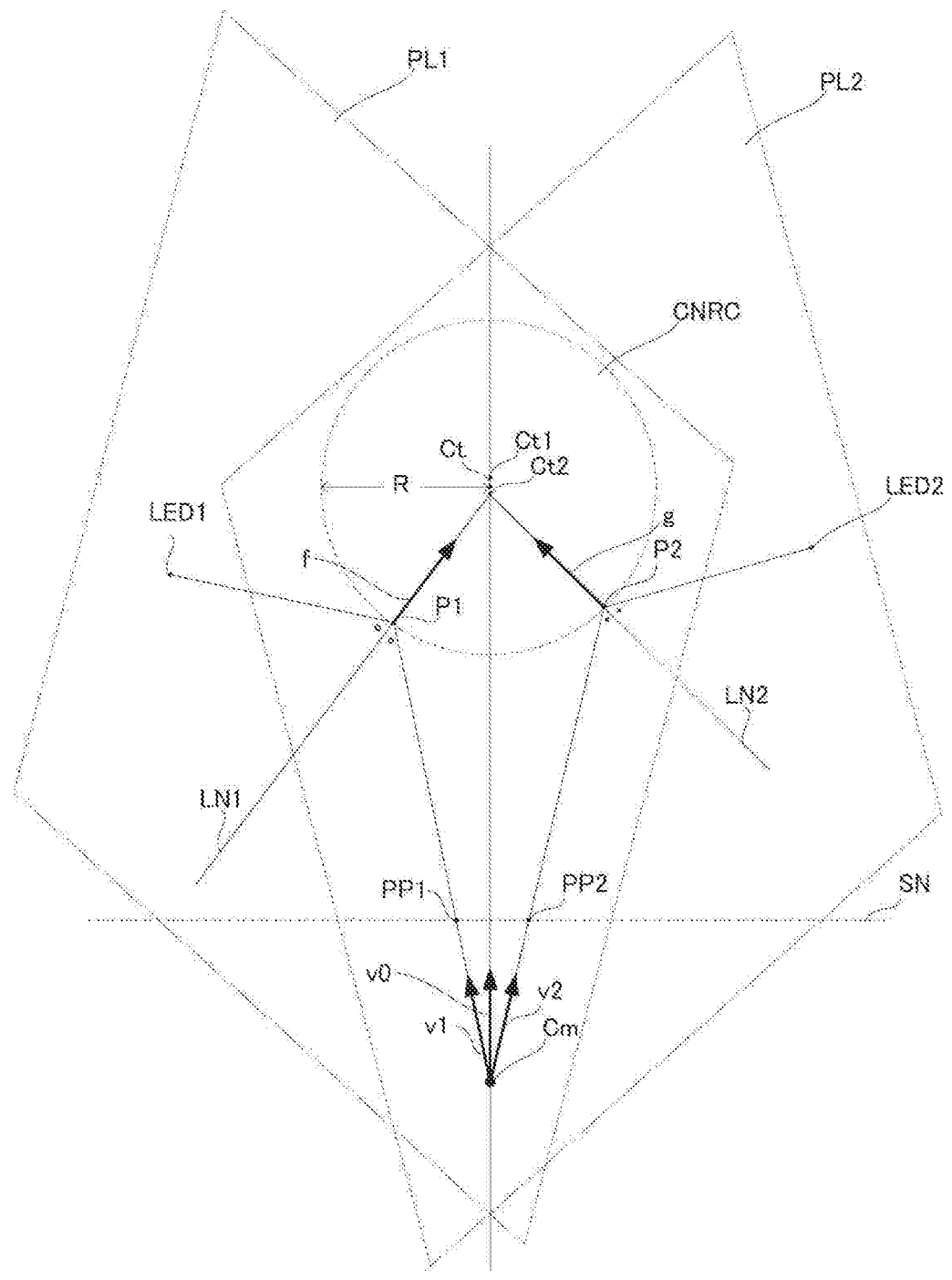
FIG. 9 is a diagram illustrating a principle of an optical axis calculation method according to a first embodiment.

FIG. 9 is a diagram illustrating the principle of the method of the optical axis calculation according to the first embodiment.

In FIG. 9, a corneal curvature ball CNRC having a curvature the same as that of the cornea is assumed, and its corneal curvature center is defined as Ct, and the radius of the corneal curvature ball CNRC is defined as R, and the optical center of a camera is defined as Cm.

In addition, each of a first LED and a second LED is regarded as a point light source, and the position of the IR lighting device LD1 is defined as LED1, and the position of the IR lighting device LD2 is defined as LED2.

In addition, a reflection image position of the IR lighting device LD1 in a three dimensional space is defined as P1, and a reflection image position of the IR lighting device LD2 in a three dimensional space is defined as P2.

At this time, if a plane that includes the position LED1 of the IR lighting device LD1, the reflection image position P1, and the optical center Cm of the camera is defined as PL1, and a plane that includes the position LED2 of the IR lighting device LD2, the reflection image position P2, and the optical center Cm of the camera is defined as PL2, then an intersection line CL of the plane PL1 and the plane PL2 passes through the corneal curvature center Ct.

Therefore, a unit vector from the optical center Cm of the camera toward the corneal curvature center Ct on the intersection line CL is defined as v0, and a unit vector from the optical center Cm of the camera toward the reflection image position P1 on the plane PL1 is defined as v1, and a unit vector from the optical center Cm of the camera toward the reflection image position P2 on the plane PL2 is defined as v2.

In addition, a vector from the reflection image position P1 toward the corneal curvature center Ct on the plane PL1 is defined as f, and a vector from the reflection image position P2 toward the corneal curvature center Ct on the plane PL2 is defined as g.

From the conditions described above, the following is satisfied.

(1) The corneal curvature center Ct is located at a position where the unit vector v0 is multiplied by a constant t0 (t0 is a positive real number). Therefore, in the description below, it is assumed that a corneal curvature center at a stage where the constant t0 is unknown is defined as a first estimated corneal curvature center Ct1.

(2) The reflection image position P1 is located at a position where the unit vector v1 is multiplied by a constant t1 (t1 is a positive real number).

(3) The reflection image position P2 is located at a position where the unit vector v2 is multiplied by a constant t2 (t2 is a positive real number).

(4) The reflection image position P1 and the reflection image position P2 are located at a distance of the corneal curvature radius R from the corneal curvature center Ct.

Figure 10:
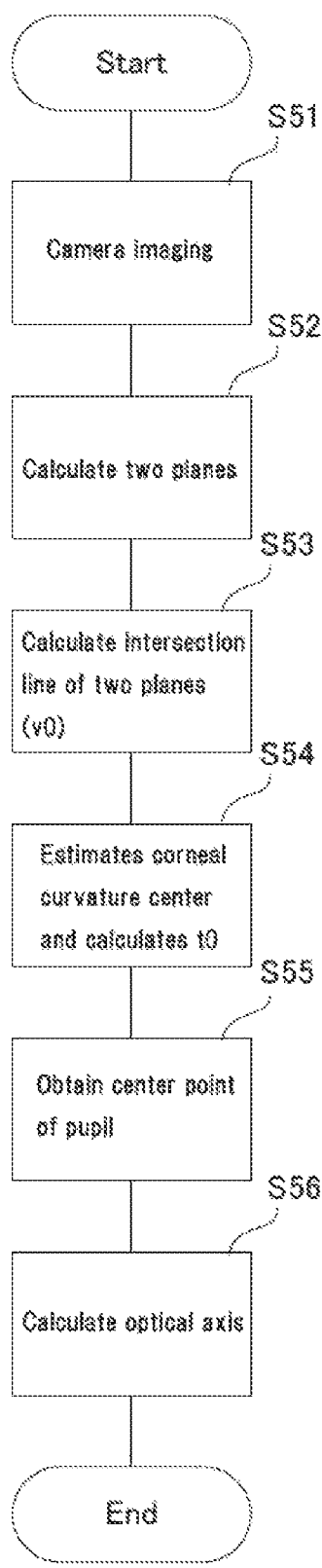
FIG. 10 is a processing flowchart of an optical axis calculation processing according to the first embodiment.

FIG. 10 is a processing flowchart of an optical axis calculation processing.

Initially, the MPU 31 of the operator unit 12 controls the IR lighting device LD1 and the IR lighting device LD2 respectively to emit the test light L, through the control interface 36 and the control interface 28, and further controls the eyeball cameras 23R and 23L to image the eyeballs (Step S51).

Subsequently, the MPU 31 of the operator unit 12 sets the radius R of the corneal curvature ball CNRC to a predetermined value, and calculates the reflection image position P1 and the reflection image position P2.

Then, the MPU 31 of the operator unit 12 calculates the plane PL1 that includes the position LED1 of the IR lighting device LD1, the reflection image position P1, and the optical center Cm of the camera. The MPU 31 then calculates the plane PL2 that includes the position LED2 of the IR lighting device LD2, the reflection image position P2, and the optical center Cm of the camera (Step S52).

From the plane PL1 (equation that expresses the plane PL1) and the plane PL1 (equation that expresses the plane PL2), the MPU 31 of the operator unit 12 calculates an intersection line of the two planes (Step S53).

In addition, the MPU 31 of the operator unit 12 calculates the unit vector v1 from the reflection image position P1 described above, and then obtains the vector f from the calculated unit vector v1, the reflection image position P1, and the position LED1 of the IR lighting device LD1.

In addition, the MPU 31 of the operator unit 12 calculates the unit vector v2 from the reflection image position P2 described above, and then obtains the vector g from the calculated unit vector v2, the reflection image position P2, and the position LED2 of the IR lighting device LD2.

Then, the MPU 31 of the operator unit 12 estimates the position of the corneal curvature center, and calculates the constant t0 (Step S54).

Initially, the MPU 31 of the operator unit 12 assumes a first straight line LN1 along the orientation of the vector f from the reflection position P1, and assumes a second straight line LN1 along the orientation of the vector g from the reflection image position P2, and then calculates an intersection point of the straight line LN1 and the straight line LN2 (or a point closest to both of the two straight lines (nearest neighbor point), and defines it as a second estimated corneal curvature center Ct2.

In this case, the first estimated corneal curvature center Ct1 and the second estimated corneal curvature center Ct2 should actually be equal to each other, and thus the constant t0 can be calculated such that the equation below is minimized.

$$|Ct1-Ct2|$$

Hereinafter, the constant t0 is calculated based on the principle described above.

Initially, the MPU 31 of the operator unit 12 calculates the unit vector v0, based on the intersection line of the two planes PL1 and PL2.

More specifically, when a vector v01 having the same orientation as the unit vector v0 is assumed, the equation below is satisfied.

$$v01=\{(LED1-Cm)\times(PP1-Cm)\}\times\{(LED2-Cm)\times(PP2-Cm)\}$$

In the equation, PP1 is the position on an imaging sensor of the camera at the reflection image position P1, and PP2 is the position on the imaging sensor of the camera at the reflection image position P2.

Then the unit vector v0 can be expressed by the equation below:

$$v0=v01/\|v01\|,$$

where, $\|v01\|$ is the magnitude (scalar) of the v01.

Then, the MPU 31 of the operator unit 12 calculates the unit vector v1 and the unit vector v2, from the optical center Cm of the camera, the position PP1, and the position PP2.

$$v1=(Cm-PP1)/\|Cm-PP1\|$$

$$v2=(Cm-PP2)/\|Cm-PP2\|$$

The first estimated corneal curvature center Ct1 corresponding to the corneal curvature center Ct should be located at a position where the unit vector v0 is multiplied by the constant t0, when the optical center Cm of the camera is defined as a base point. Therefore, the equation below is satisfied.

$$Ct1=t0\cdot v0+Cm$$

In addition, the reflection image position P1 and the reflection image position P2 are calculated on the assumption that the reflection image position P1 is located at a position where the unit vector v1 is multiplied by the constant t1, by using the optical center Cm of the camera is defined as a base point; and the reflection image position P2 is located at a position where the unit vector v2 is multiplied by a constant t2, by using the optical center Cm of the camera is defined as a base point; and the reflection image position P1 and the reflection image position P2 are located at a distance of the corneal curvature radius R from the corneal curvature center Ct.

More specifically, as follows.

If $P1 = t1 \cdot v1 + Cm$, then $R^2 = \|t0 \cdot v0\|^2 + \|t1 \cdot v1\|^2 - 2 \cdot t0 \cdot t1 \cdot v0 \cdot v1$, which results in the equation below:

$t1 = t0 \cdot v0 \cdot v1 \pm \sqrt{\{(\|v0 \cdot v1\|^2 - 1) \cdot t0^2 + R^2\}}$ In the equation, the positive sign (+) in the double sign (±) corresponds to an intersection point located backward as viewed from the camera, among two intersection points at which a sphere having a radius R centering at the corneal curvature center Ct intersects a straight line passing through the optical center Cm of the camera and the reflection image position P1. Therefore, the negative sign (−) that corresponds to the intersection point located forward as viewed from the camera is the constant t1 to be obtained.

Similarly, if $P2 = t2 \cdot v2 + Cm$, then $R^2 = \|t0 \cdot v0\|^2 + \|t2 \cdot v2\|^2 - 2 \cdot t0 \cdot t2 \cdot v0 \cdot v2$. This results in the equation below:

$t2 = t0 \cdot v0 \cdot v2 \pm \sqrt{\{(\|v0 \cdot v2\|^2 - 1) \cdot t0^2 + R^2\}}$ Also in this case, the positive sign (+) in the double sign (±) corresponds to the intersection point located backward as viewed from the camera, among the two intersection points, at which the sphere having the radius R centering at the corneal curvature center Ct intersects a straight line passing through the optical center Cm of the camera and the reflection image position P2. Therefore, the negative sign (−) that corresponds to the intersection point located forward as viewed from the camera is the constant t2 to be obtained.

Subsequently, the vector f and vector g are obtained.

From the relationship among the unit vector v1 and the reflection image position P1 and the first LED position LED1, and the relationship among the unit vector v2 and the reflection image position P2 and the second LED position LED2, equations below can be obtained:

$f = v1 + (P1 - LED1)/\|P1 - LED1\|$ $g = v2 + (P2 - LED2)/\|P2 - LED2\|$

Subsequently, the MPU 31 of the operator unit 12 assumes a first straight line LN1 passing through the reflection image position P1 and along the orientation of the vector f, and assumes a second straight line LN2 passing through the reflection image position P2 and along the orientation of the vector g. Then, an intersection point of the straight line LN1 and the straight line LN2 (or the closest point from both of the two straight lines (nearest neighbor point)) is calculated, and defined as a second estimated corneal curvature center Ct2.

$$Ct2 = \frac{1}{2}[f \cdot g]\begin{bmatrix} \|f \cdot f\| & -\|f \cdot g\| \\ -\|f \cdot g\| & \|g \cdot g\| \end{bmatrix}^{-1}\begin{bmatrix} -f \cdot (P1 - P2) \\ g \cdot (P1 - P2)) \end{bmatrix} + \frac{1}{2}(P1 + P2)$$ [Equation 1]

In this case, the first estimated corneal curvature center Ct1 and the second estimated corneal curvature center Ct2 should be equal to the corneal curvature center Ct, respectively. Therefore, the difference between the first estimated corneal curvature center Ct1 and the second estimated corneal curvature center Ct2 is defined as an evaluation value X, and a constant t0 that minimizes the evaluation value X is calculated.

In other words, the constant t0 that satisfies the equation below is calculated.

$X = \arg_{t0}^{min} \|Ct1 - Ct2\|^2$ [Equation 2]

Once the constant t0 is calculated, the MPU 31 of the operator unit 12 obtains the center point of the pupil, based on the captured image taken by the eyeball camera 23R (Step S55).

Then, the MPU 31 calculates the optical axis of the right eye, by connecting the center point of the pupil, and the corneal curvature center Ct calculated by the constant t0 and the unit vector v0 (Step S56).

Next, processing is described referring again to FIGS. 7 and 8.

As described above, after the gaze image GT to be gazed at by the test subject by using the right eye is displayed (Step S41) and the optical axis of the right eye is calculated, the MPU 31 of the operator unit 12 calculates a difference between the optical axis calculated in Step S56 and the visual axis, as a correction amount (step S43).

More specifically, the MPU 31 of the operator unit 12 calculates the difference between the calculated optical axis and the visual axis (line of vision) of the test subject as a correction amount, such that the calculated position of the optical axis coincides with the visual axis (line of vision) of the test subject who is gazing at the gaze image GT. In other words, the MPU 31 calculates the difference between the calculated optical axis position and the visual axis (line of vision) of the test subject as the correction amount, such that the display position of the visual axis mark image GVA (which corresponds to the calculated optical axis position) coincides with the gaze image GT (which corresponds to the visual axis (line of vision) of the test subject).

As a result, an image after the calibration is performed is displayed on the operator display 37, as illustrated in FIG. 7C. In other words, a screen in which the display position of the visual axis mark image GVA coincides with the display position of the gaze image GT is displayed on the operator display 37.

In this state, the operator determines whether or not the display position of the visual axis mark image GVA coincides with the display position of the gaze image GT. If the parameter at the time of the visual axis calculation is not optimized and thus the display position of the visual axis mark image GVA does not coincide with the display position of the gaze image GT, then the operator instructs to perform a similar calibration again.

After the calibration is completed, the MPU 31 of the operator unit 12 would perform calculation of an optical axis as needed, and correct the calculated optical axis by the correction amount obtained in Step S43, and then estimate a visual axis of the test subject as needed (Step S44).

As a result, based on the estimated visual axis of the right eye as needed, the MPU 31 of the operator unit 12 would display a visual axis mark image GVA at a position corresponding to the estimated position of the visual axis onto the operator display 37 as needed.

In this case, if the visual axis mark image GVA stays within a predetermined range for a predetermined time, then a calibration may be performed so that the display position (calculated optical axis position) of the visual axis mark image GVA coincides with the gaze image GT (visual axis (line of vision) of the test subject), assuming that the position the visual axis mark image GVA stayed is the gaze position.

{4} Second Visual Axis Calibration

If the display position of the visual axis mark image GVA coincides with the display position of the gaze image GT, and the calibration of the visual axis of the right eye, i.e., the calibration of the first visual axis, is completed, then a calibration of the visual axis of the left eye as a second visual axis is similarly performed as a second visual axis calibration. Description is made below referring again to FIG. 8.

Figure 11:
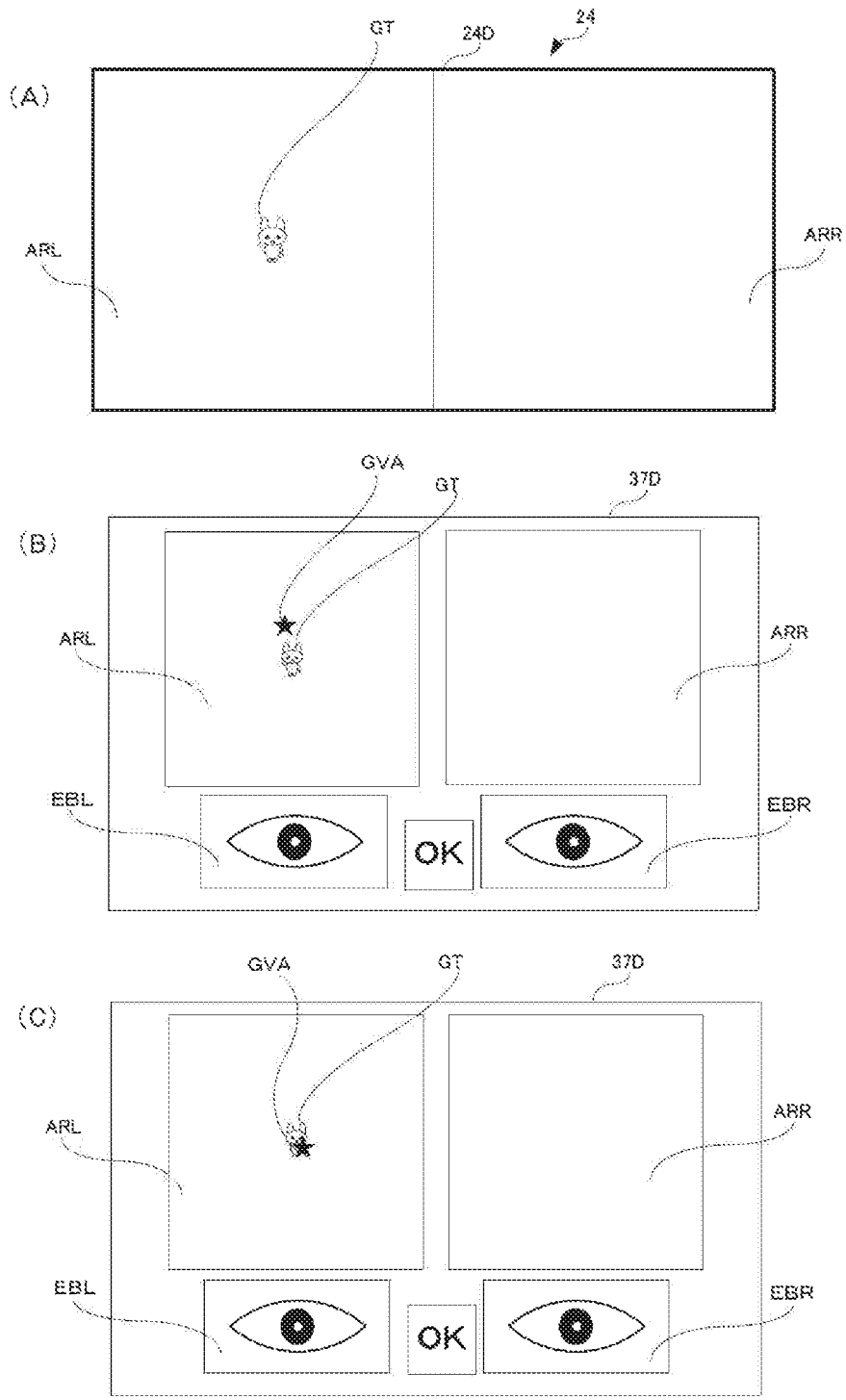
FIG. 11 is a diagram illustrating a visual axis calibration of the left eye.

FIG. 11 is a diagram illustrating the visual axis calibration of the left eye.

When the operator operates a keyboard or a mouse to instruct a processing for determining the visual axis of the left eye, the MPU 31 of the operator unit 12 displays the gaze image GT to be gazed at by the test subject using the left eye is displayed on the left eye image display area ARL of the display screen of the test subject display 24, as illustrated in FIG. 11A, through the multimedia interface 35 and the multimedia interface 25 and the sound/image separation portion 26 (Step S41).

At this time, the operator prompts the test subject to gaze at the gaze image GT, in order to restrict changes in the position of the visual axis (line of vision) of the test subject.

Then, the MPU 31 of the operator unit 12 calculates the optical axis of the left eye, with the changes in the visual axis of the left eye being restricted (Step S42).

When the optical axis of the left eye is calculated, the MPU 31 of the operator unit 12 displays an estimated optical axis position onto the display screen 37D of the operator display 37, as a display position of the visual axis mark image GVA.

If the gaze image GT does not coincide with the visual axis mark image GVA as illustrated in FIG. 11B, then the operator operates the mouse to instruct a calibration. The MPU 31 of the operator unit 12 then performs the calibration such that the visual axis mark image GVA coincides with the gazing image GT (Step S43).

After the calibration is completed, the MPU 31 would calculate the optical axis as needed, and correct the calculated optical axis by the correction amount obtained in Step S43, and then estimate the visual axis of the test subject as needed (Step S44).

Also in this case, if the visual axis mark image GVA stays within a predetermined range for a predetermined time, then the MPU 31 of the operator unit 12 may perform a calibration such that the display position (calculated optical axis position) of the visual axis mark image GVA coincides with the gaze image GT (visual axis (line of vision) of the test subject), assuming that the position the visual axis mark image GVA stayed is the gaze position.

{5} Visual Function Test

Subsequently, a processing is described where a nine gaze directions test (Hess chart) is performed as a visual function test.

Figure 12:
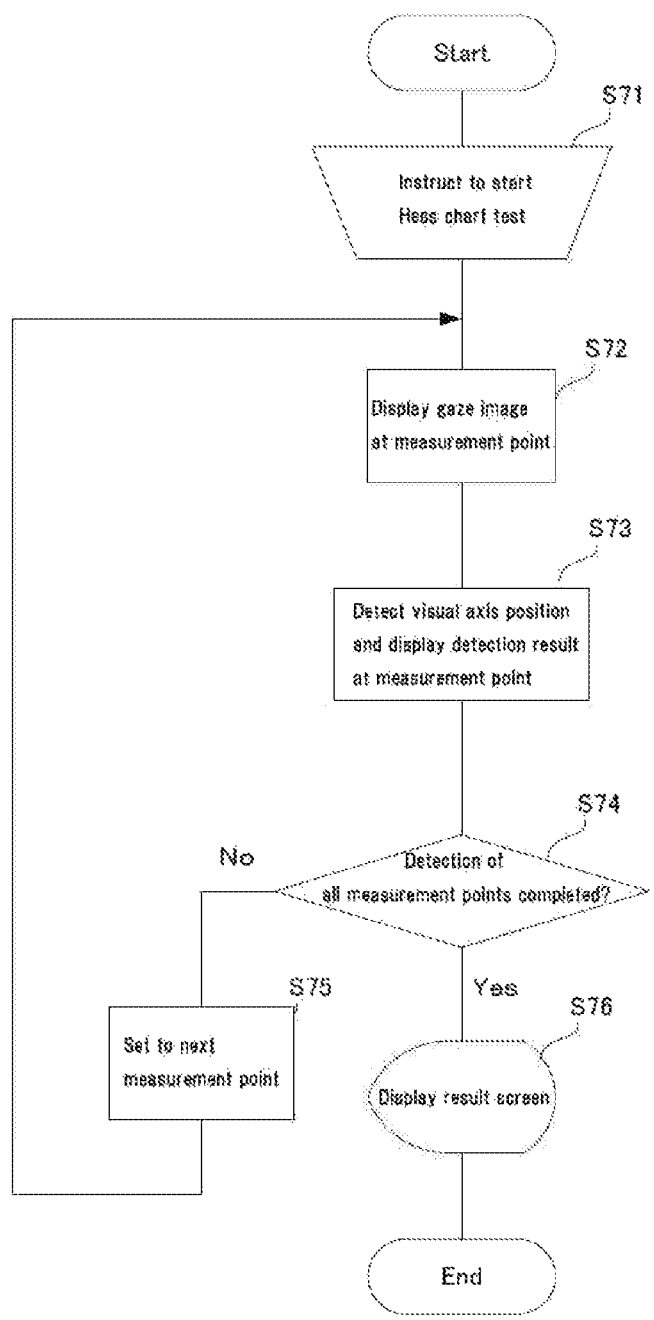
FIG. 12 is a processing flowchart at the time of a nine gaze directions test.

FIG. 12 is a processing flowchart in a nine gaze directions test.

{5.1} First Visual Function Test

After the visual axis calibration of the right eye and the left eye is completed, the operator initially instructs to start a nine gaze directions test of the right eye, using a mouse or a keyboard (Step S71).

Figure 13:
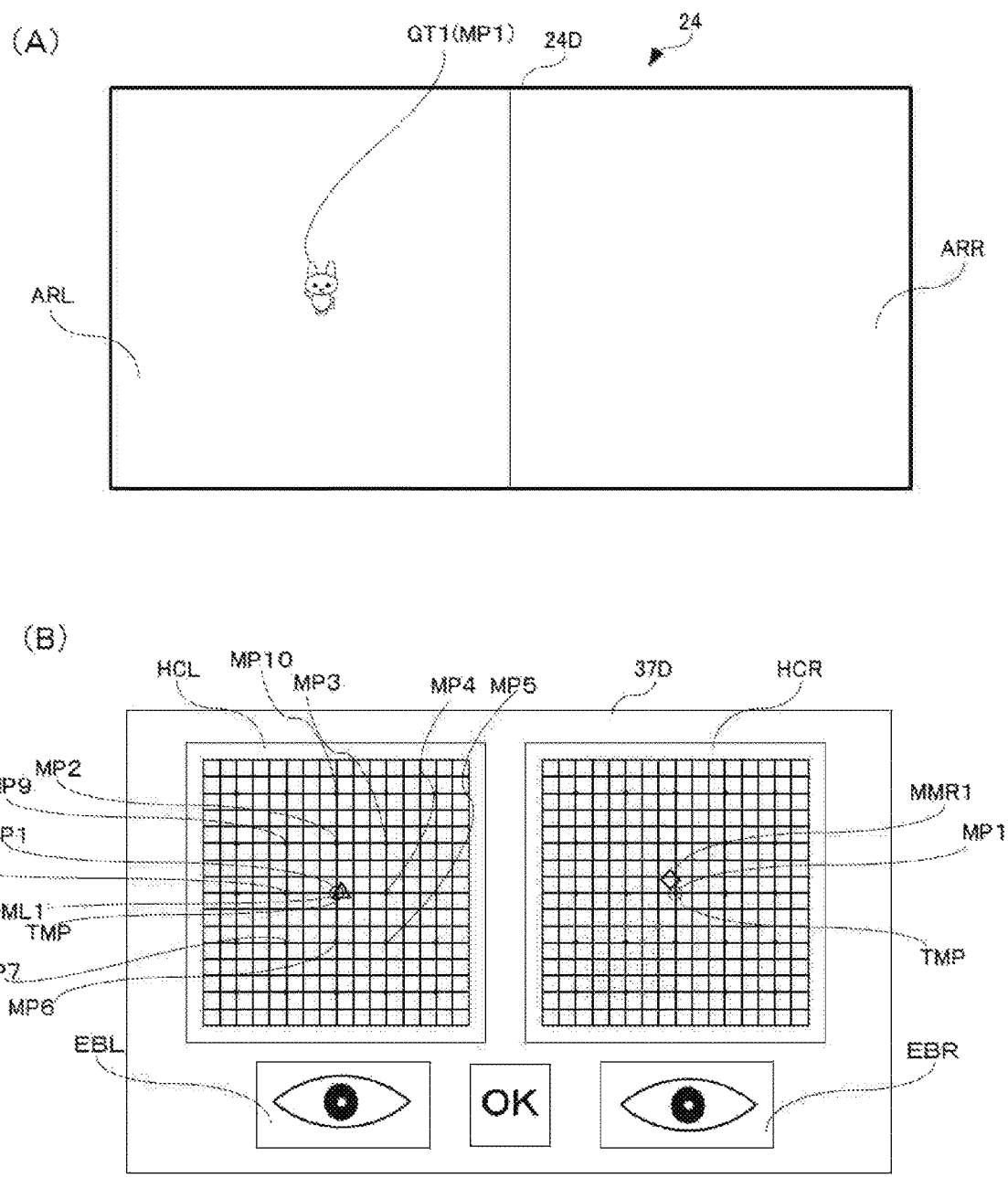
FIG. 13 is a diagram illustrating an example (first example) of a display screen on an operator display at the time of a nine gaze directions test of the right eye.

FIG. 13 is a diagram illustrating an example (first example) of a display screen in a nine gaze directions test of the right eye in an operator display.

When the start of the nine gaze directions test of the right eye is instructed, the MPU 31 of the operator unit 12 displays a gaze image GT1 at a position that corresponds to a measurement point MP1 at the center of the nine gaze directions test chart (Hess chart) in a left eye image display area of the test subject display 24, and an arbitrary color is displayed on the whole screen in the right eye image display area (Step S72).

On the display screen 24D of the test subject display 24, only the gaze image GT1 is displayed, and the nine gaze directions test eye position chart is not displayed. Therefore, the test subject can concentrate on the test without being distracted, compared to a conventional case where the test subject needs to gaze at a measurement point in the nine gaze directions test chart. The measurement accuracy thus can be further improved.

In this state, the operator directs the test subject to gaze at the gaze image GT1.

In the left image display area HCL of the display screen 37 of the operator display 37, the nine gaze directions test chart, a gaze position specifying image TMP, and a left eye gaze position image MML1 are displayed. In the right image display area, the nine gaze directions test chart, the gaze position specifying image TMP, and the gaze position image MMR1 of the right eye of the test subject are displayed.

Furthermore, in the left eyeball display area EBL and the right eyeball display area EBR at a lower portion of the display screen 37D of the operator display 37, a captured image of the eyeball of the test subject is displayed.

In parallel with these operations, the MPU 31 of the operator unit 12 determines whether the center positions of the gaze position image MML1 of the left eye and the gaze position image MMR1 of the right eye stay within a predetermined stay range for a predetermined stay time. If it is determined they stayed, the center positions are acquired as measurement data corresponding to the measurement point MP1, and the same image (or a predetermined measurement mark image) as the gaze position images MML1 and MMR1 is displayed as a measurement mark (Step S73).

When acquisition of measurement data that corresponds to the measurement point MP1 is completed, the MPU 31 of the operator unit 12 determines whether or not the measurement for all measurement points (=MP1 (first measurement) to MP9, MP1 (second measurement]) is completed (Step S74).

In the determination in Step S74, the measurement is not completed at this moment, and thus the MPU 31 of the operator unit 12 sets the measurement point MP2 at 15° as a next measurement point, proceeds the processing back to Step S72, and obtains measurement data similarly.

Figure 14:
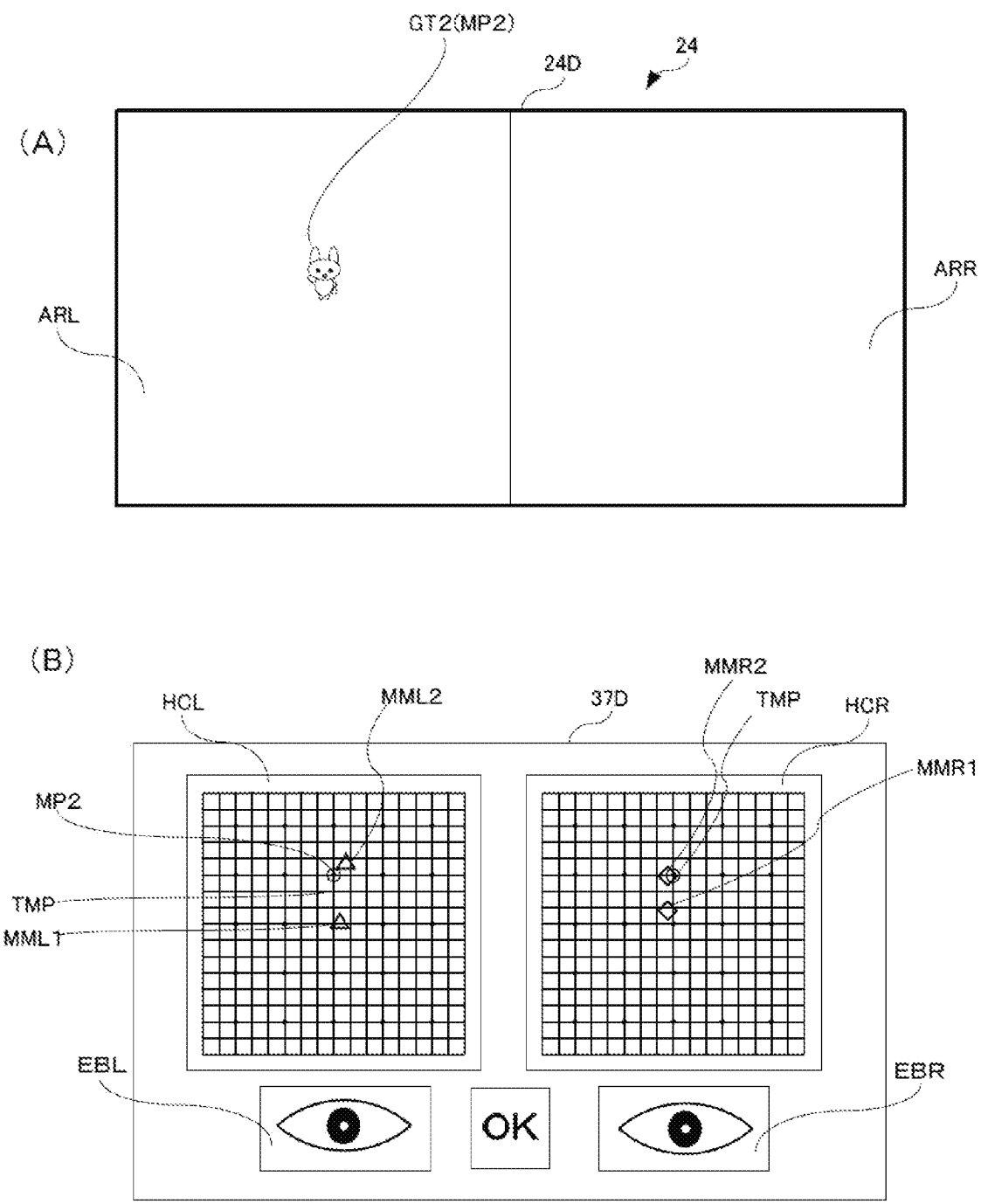
FIG. 14 is a diagram illustrating an example (second example) of a display screen on an operator display at the time of a nine gaze directions test of the right eye.

FIG. 14 is a diagram illustrating an example (second example) of a display screen in the operator display in the nine gaze directions test of the right eye.

In the left image display area HCL of the display screen 37 of the operator display 37, the nine gaze directions test chart, the gaze position specifying image TMP, and a left eye gaze position image MML2 are displayed. In the right image display area of the display screen 37 of the operator display 37, the nine gaze directions test chart, the gaze position specifying image TMP, and a gaze position image MMR2 of the right eye of the test subject are displayed.

In the left eyeball display area EBL and the right eyeball display area EBR at a lower portion of the display screen 37D of the operator display 37, a captured image of the eyeball of the test subject is displayed.

In parallel to these operations, the MPU 31 of the operator unit 12 determines whether or not the center positions of the left eye gaze position image MML2 and the right eye gaze position image MMR2 stay within a predetermined stay range for a predetermined stay time. If it is determined that they stayed, the center positions are acquired as measurement data that corresponds to the measurement point MP2, and then the measurement mark MML2 is displayed.

After the acquisition of the measurement data that corresponds to the measurement point MP2 is completed, the MPU 31 of the operator unit 12 similarly acquires measurement data for the measurement points MP3 to MP9 at 15° (Steps S72 to S74).

When the acquisition of measurement data of the measurement point MP9 is completed, the MPU 31 of the operator unit 12 displays again the gage image GT1 at the measurement point MP1, and acquires measurement data similarly.

In the determination in Step S74, if it is determined that the measurement is completed ("Yes" in Step S74), then the MPU 31 of the operator unit 12 displays a measurement result figure, in which the measurement point MP1 (first measurement), the measurement point MP2, . . . , the measurement point MP9, and the measurement point MP1 (second measurement) are sequentially connected in this order with a straight line (Step S76).

In this case, if the first measurement of the measurement point MP1 differs from the second measurement of the measurement point MP1 by a predetermined threshold difference or more, then a test is performed again as a retest.

The MPU 31 of the operator unit 12 displays onto the display screen of the operator display a screen for inquiring whether or not abnormality, for example due to a light paralysis or the like, is detected. If it is determined that abnormality is not detected, then the MPU 31 of the operator unit 12 acquires data also for the measurement points at 30°, similarly to the measurement points MP1 to MP9 at 15°.

{5.2} Second Visual Function Test

When the nine gaze directions test of the right eye as the first visual function test is completed, the operator instructs to start a nine gaze directions test of the left eye, as a second visual function test (Step 71), similarly to the procedures in Steps S72 to Step S76 described above, to complete the nine gaze directions test of the left eye as the second visual function test.

{6} Test Result Representation

Figure 15:
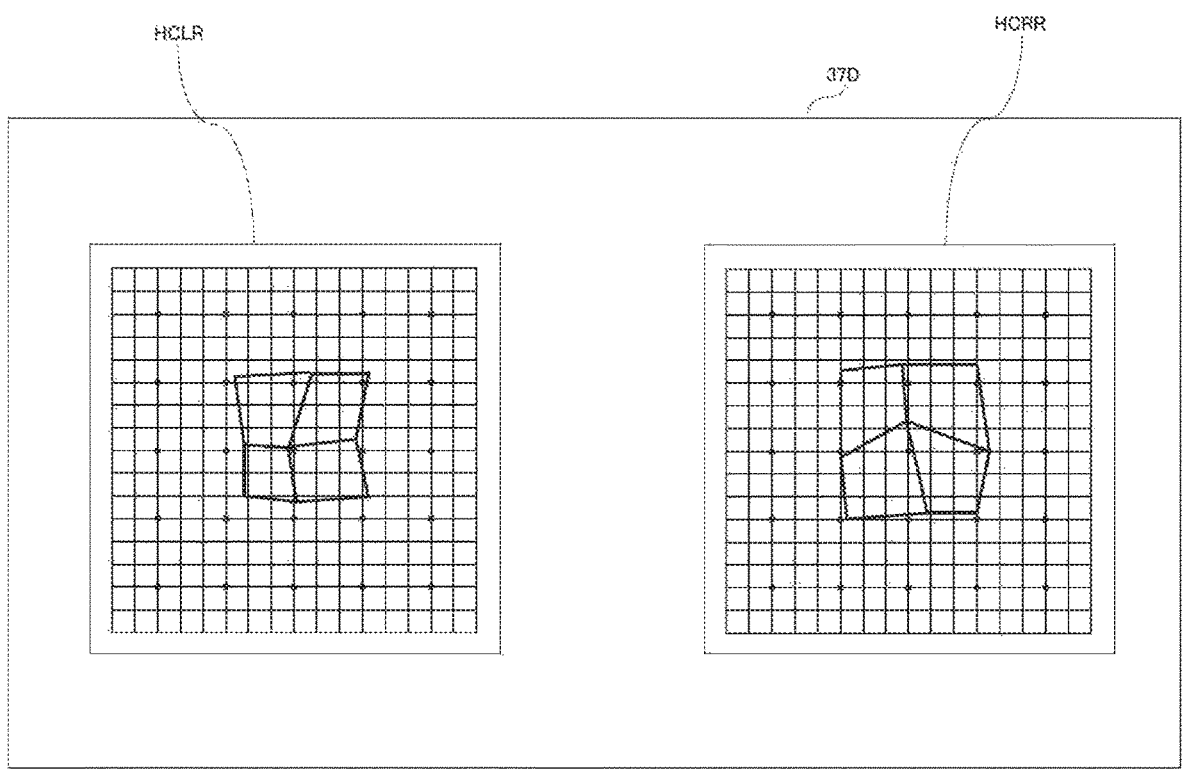
FIG. 15 is a diagram illustrating a display example (first example) of a measurement result figure.

FIG. 15 is a diagram illustrating a display example (first example) of a measurement result figure.

When the first measurement at the measurement point MP1 and the second measurement at the measurement point MP1 are within a predetermined threshold difference, the MPU 31 of the operator unit 12 determines that the measurement result is reliable, and displays a measurement result figure, in which the measurement point MP1 (first measurement), the measurement point MP2, . . . , the measurement point MP9, and the measurement point MP1 (second measurement) are connected sequentially in this order with a straight line.

More specifically, in the example in FIG. 15, a left eye nine gaze directions test result screen HCLR that corresponds to the left eye is displayed on the left side of the display screen 37D of the operator display 37. Similarly, a right eye nine gaze directions test result screen HCRR that corresponds to the right eye is displayed on the right side of the display screen 37D of the operator display 37.

According to the display example illustrated in FIG. 15, a display similar to a conventional nine gaze directions test result on a sheet of paper is provided. By printing it to a printer 38, a chart similar to the conventional one can be obtained.

Figure 16:
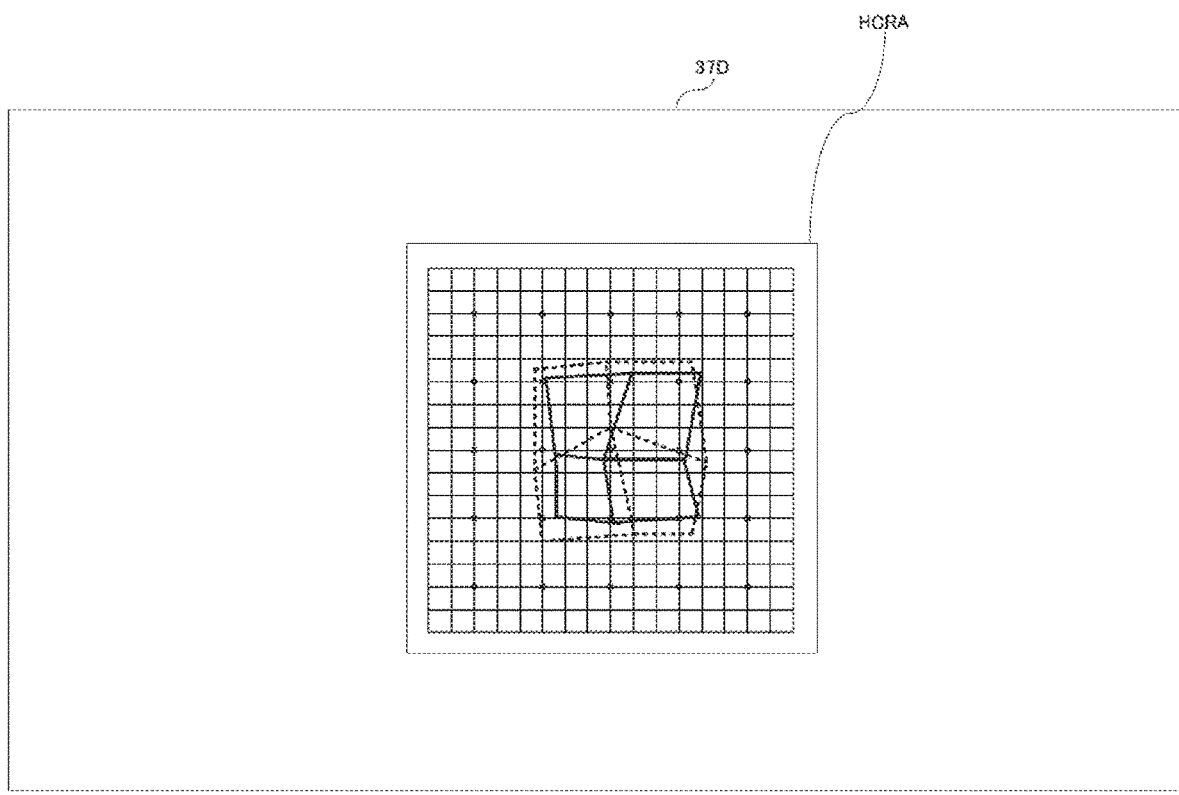
FIG. 16 is a diagram illustrating a display example (second example) of a measurement result figure.

FIG. 16 is a diagram illustrating a display example (second example) of a measurement result figure.

In the case illustrated in FIG. 15, it is not easy to visually compare the nine gaze directions test results for both eyes. However, the comparison can be easily done by displaying the nine gaze directions test results for both eyes on a single both-eyes nine gaze directions test result screen HCRA, as illustrated in FIG. 16.

As described above, according to the first embodiment, an operator who is an examiner can easily recognize which position is actually viewed by the test subject as a gaze position. Therefore, the operator can make the test subject surely gaze at the gaze position as instructed by the examiner during the test, and thus the reliability of the test can be easily ensured.

Consequently, even when an infant or the like is to be examined, the operator can reliably recognize whether or not the infant follows the operator's instruction.

[1.1] Modification Example of the First Embodiment

In the description above, the calibration of the visual axis is performed separately for the left eye and the right eye. However, this modification example is for performing the visual axis calibration of the left and right eyes at the same time.

Figure 17:
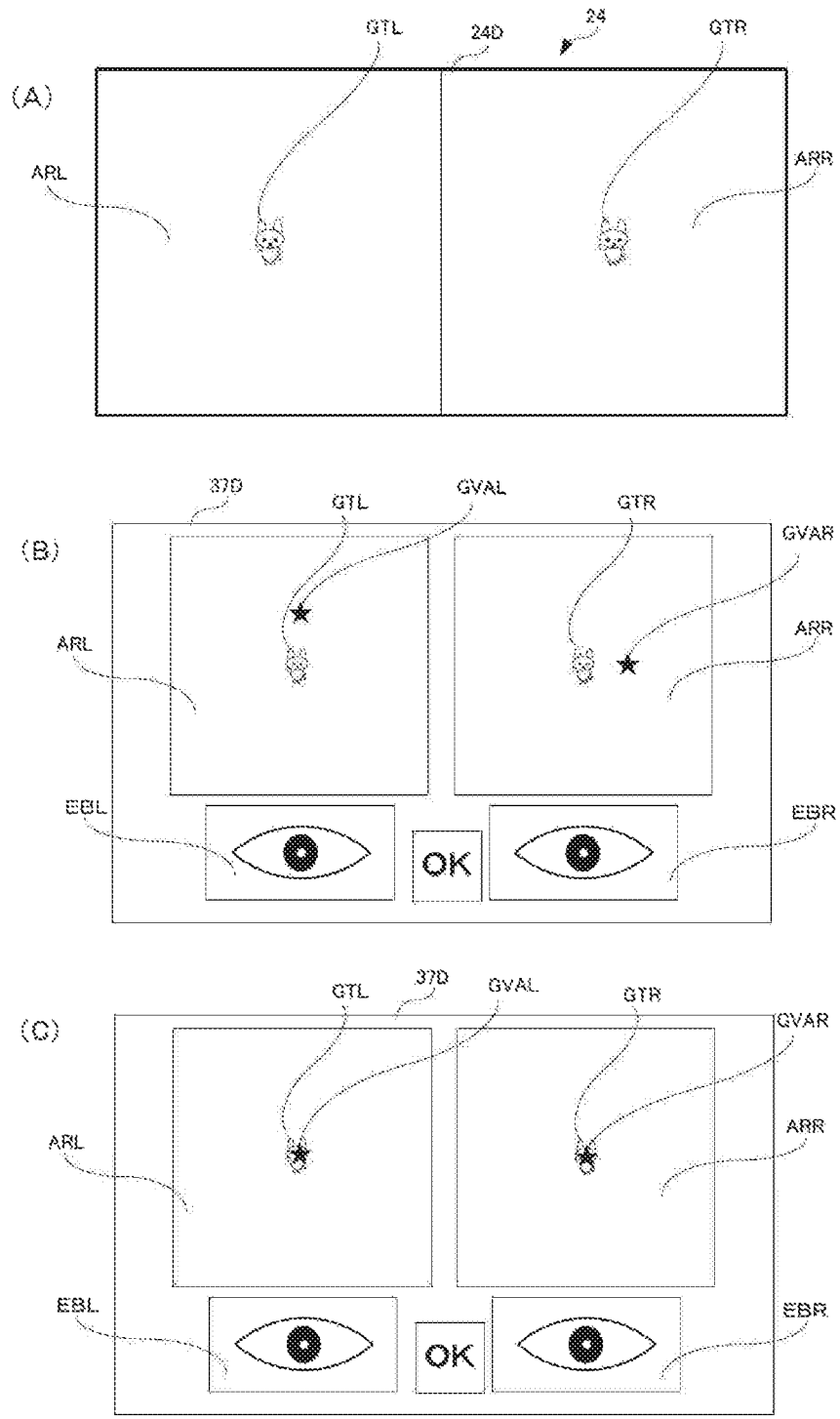
FIG. 17 is a diagram illustrating a simultaneous right-and-left eyes visual axis calibration processing.

FIG. 17 is a diagram illustrating a right-and-left eyes simultaneous visual axis calibration processing.

When the operator operates a keyboard or a mouse to instruct to perform a processing for determining the visual axis of the right eye, the MPU 31 of the operator unit 12 displays a gage image GTR to be gazed at by the test subject using the right eye, in the right eye image display area ARR of the display screen 24D of the test subject display 24, and displays a gaze image GTL to be gazed at by the test subject using the left eye, in the left eye image display area ARL, as illustrated in FIG. 17A, through the multimedia interface 35, the multimedia interface 25, and the audio/video separation unit 26.

At this time, the operator prompts the test subject to gaze at the gaze images GTR and GTL.

Then, the MPU 31 of the operator unit 12 performs a visual axis estimation of the right and left eyes.

Accordingly, the MPU 31 of the operator unit 12 displays the positions of the visual axes onto the operator display 37 as visual axis mark images GVAR and GVAL, based on the estimated visual axes of the right eye and the left eye.

If the gaze image GTR does not coincide with the visual axis mark image GVAR as illustrated in FIG. 17B, then the operator operates the mouse to instruct a calibration, and the MPU 31 of the operator unit 12 performs the calibration such that the visual axis mark image GVAR coincides with the image GTR, as illustrated in FIG. 17C.

Similarly, if the gaze image GTL does not coincide with the visual the view mark image GVAL as illustrated in FIG. 17B, then the operator operates the mouse to instruct a calibration, and the MPU 31 of the operator unit 12 performs the calibration such that the visual axis mark image GVAL coincides with the gaze image GTL, as illustrated in FIG. 17C.

As described above, according to this modification example, it is possible to simultaneously calibrate the visual axes for both eyes, which can contribute to shortened test time.

In the description above, the calibration is performed such that the visual axis mark image coincides with the gaze image when the operator operates the mouse to instruct the calibration, if the gaze image does not coincide with the visual axis mark image. However, if the visual axis mark image stayed within a predetermined range for a predetermined time, a calibration may be performed such that the visual axis mark image coincides with the gaze image, assuming that the position the visual axis mark image stayed is the gaze position.

Figure 18:
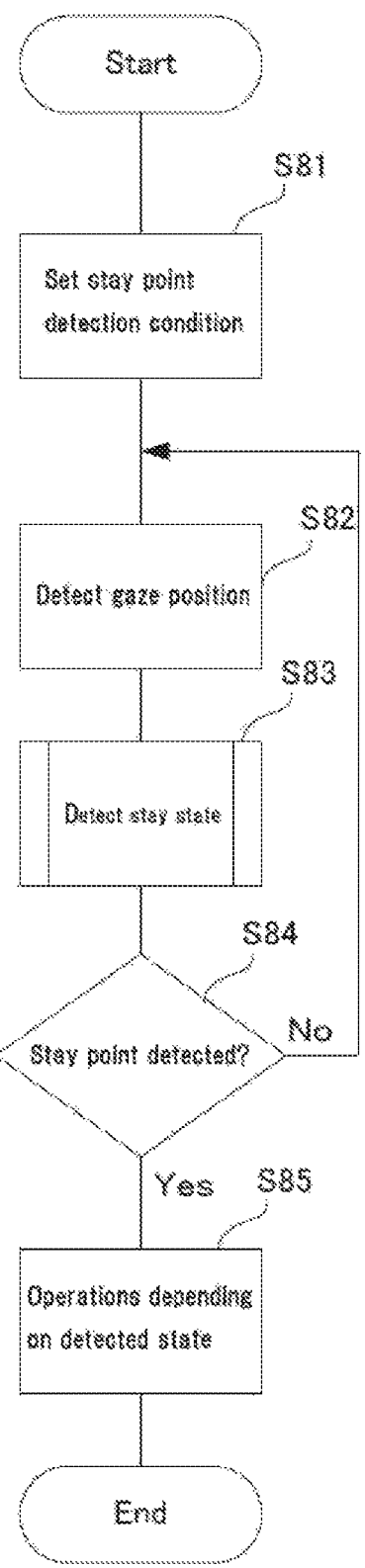
FIG. 18 is a processing flowchart of a calibration accompanying with a stay determination.

FIG. 18 is a processing flowchart of the calibration accompanied with a stay determination.

Initially, the operator or the MPU 31 of operator unit 12 sets a stay determination condition (Step S81).

The stay determination condition may include a size of a stay range, a stay time, or the like.

After the stay determination condition is set, the MPU 31 of the operator unit 12 detects a gaze position of the test subject based on an estimated visual axis of the test subject (Step S82).

Subsequently, the MPU 31 of the operator unit 12 detects a staying state of the gaze position (Step S83).

Then, the MPU 31 of the operator unit 12 determines whether or not the gaze position has stayed in the stay range, which was set as the stay determination condition, for a predetermined stay time or more (Step S84).

In the determination in Step S84, if the gaze position does not stay in the stay range that was set as the stay determination condition, or if it stayed in the stay range but only for less than the predetermined stay time ("No" in Step S84), then the processing proceeds back to Step S82, and the processing described above is performed.

In the determination of Step S84, if the gaze position stayed in the stay range, which was set as the stay determination condition, for the predetermined stay time or more ("Yes" in step S84), then an operation depending on the detected state, for example, obtaining data at a gaze point, transitioning a mode of operation, transitioning screens, or starting an audio guide, is performed (Step S85).

As described above, according to this modification example, it is possible to perform a predetermined processing without operator intervention, which may provide certain advantages such as reduction in burden of the operator in the visual function test.

[2] Second Embodiment

Figure 19:
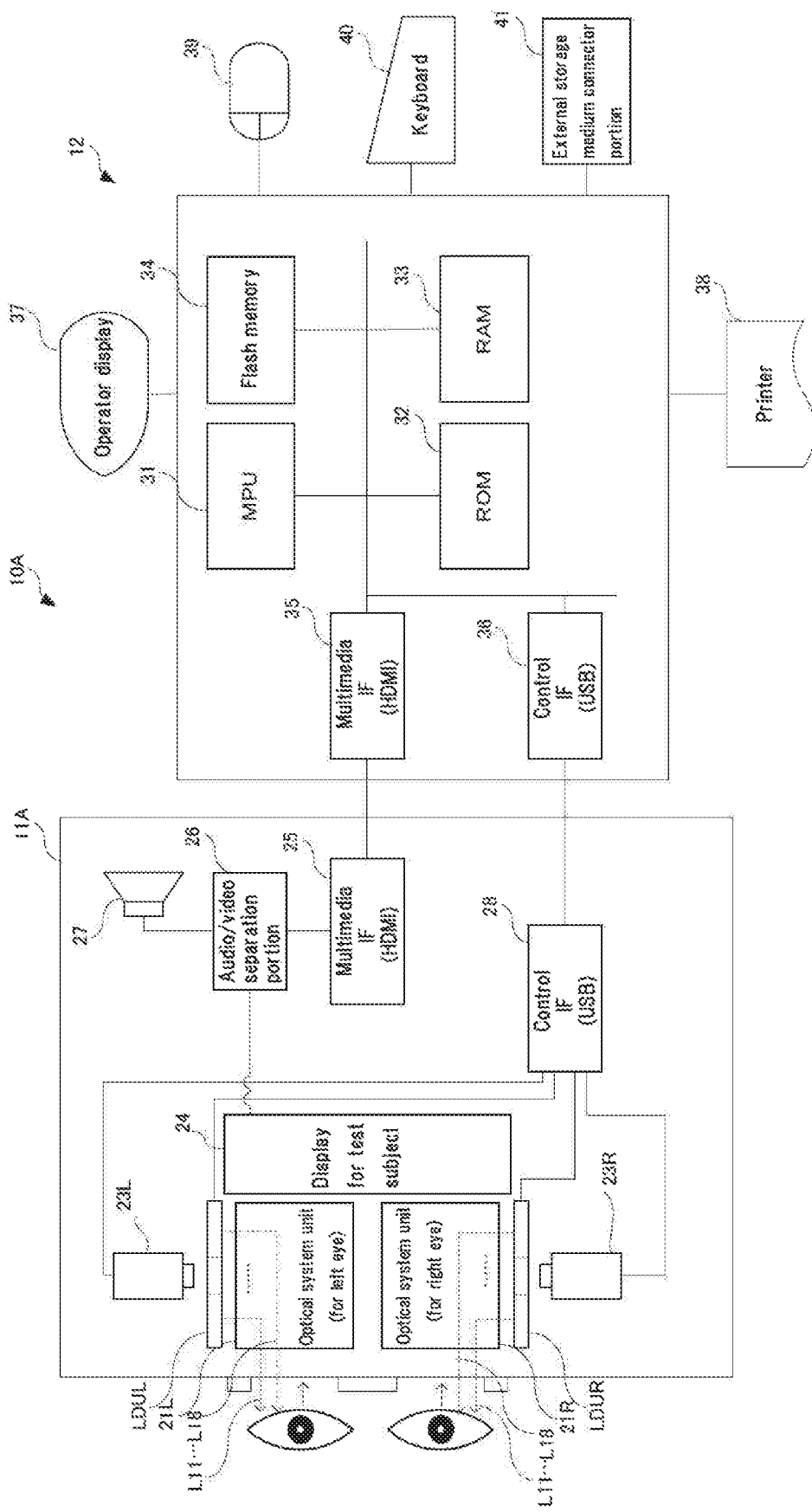
FIG. 19 is a detailed configuration block diagram of a visual function test device according to a second embodiment.

FIG. 19 is a detailed configuration block diagram of a visual function test device 10A according to a second embodiment.

A test unit 11A of the second embodiment comprises: optical system units 21R, 21L, which are capable of adjusting a viewing angle, a test distance, or the like, wherein the optical system units 21R, 21L guide infrared light (IR) test light L11 to L18 (hereinafter referred to as test light L when it is not necessary to distinguish them) to respective predetermined positions to be illuminated, and wherein the optical system units 21R, 21L each corresponds left or right eye, and guides reflected test light L to an eyeball camera that will be described later; and a pair of IR lighting unit devices LDUR and LDUL for illuminating an eyeball of the test subject using test light L, through the optical system unit 21R or the optical system unit 21L.

The test unit 11A further comprises: a pair of eyeball cameras (imaging cameras) 23R and 23L for mainly imaging an eyeball of the test subject; a test subject display 24 for displaying various images for the test subject; a multimedia interface (IF) 25, such as HDMI, for performing an interface operation of audio data and video (image) data; an audio/video separation portion 26 for performing audio/video separation of an output signal of the multimedia interface 25; a loudspeaker portion 27 for performing audio output; and a control interface (IF) 28, such as a USB, to which a control signal is input.

The operator unit 12 comprises: an MPU 31 for controlling the operator unit 12; a ROM 32 for storing control data including an operating system (OS) in a nonvolatile manner; a RAM 33 used as a working area of the MPU 31 and temporarily storing various data; a flash memory 34 for storing various data in a nonvolatile and updatable manner; a multimedia interface (IF) 35, such as HDMI, for performing an interface operation of audio data and video (image) data; and a control interface (IF) 36 for performing various interface operations for control.

The operator unit 12 further comprises: an operator display 37 connected through the multimedia interface 35, and for providing various information to the operator; a printer 38 for printing various data; a mouse 39 functioning as a pointing device and for performing various operations; a keyboard 40 for performing various operations and inputting various data; and an external storage medium connector portion 41 for connecting an external storage medium, such as a USB memory, an IC card (for example, SD card (Registered trademark)), or the like, to read data of the test subject or record test result data.

Figure 20:
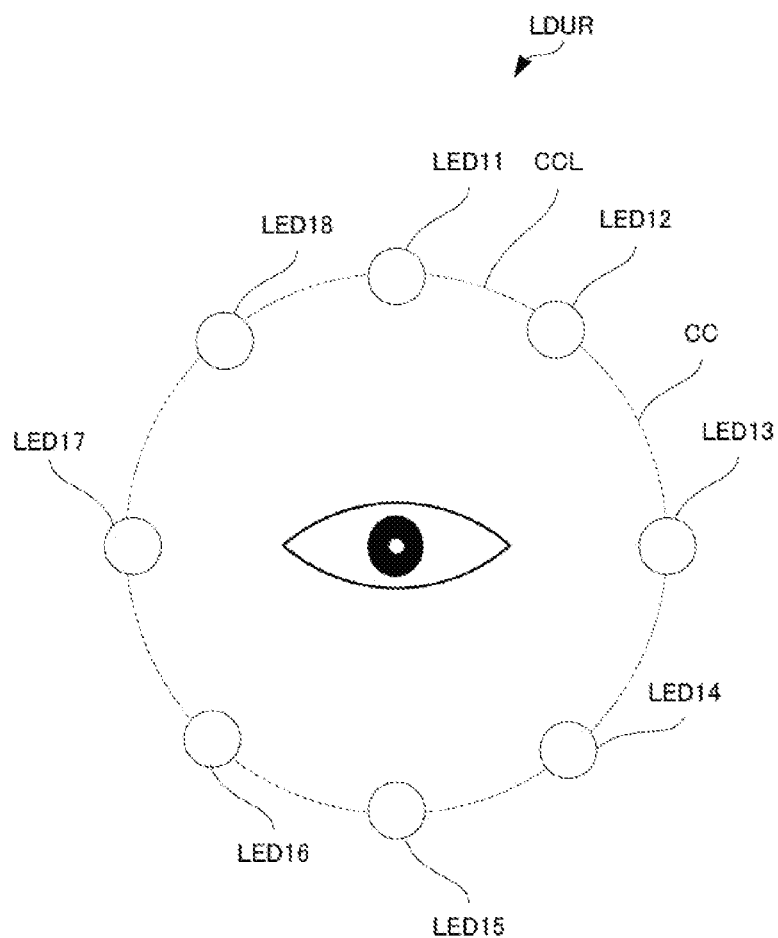
FIG. 20 is a diagram illustrating arrangement positions of LEDs in an LED unit according to the second embodiment.

FIG. 20 is a diagram illustrating arrangement positions of LEDs in an IR lighting unit device according to the second embodiment.

In this case, the IR lighting unit device LDUR and the IR lighting unit device LDUL have the same configuration, so the IR lighting unit device LDUR is described below.

The IR lighting unit device LDUR in this example comprises eight IR lighting devices, LED11 to LED18.

In this case, the IR lighting devices LED11 to LED18 are disposed on the circumference of a circle CCL on a plane that intersects the visual axis of the test subject (axis that intersects the page on the drawing) at the same angle apart (in the example in FIG. 20, at 360°/8=45° apart), as illustrated in FIG. 20. Therefore, the IR lighting device LED11 and the IR lighting device LED15, or the IR lighting device LED12 and the IR lighting device LED16, or the IR lighting device LED13 and the IR lighting device LED17, or the IR lighting device LED14 and the IR lighting device LED18 are located at 180° with respect to each other.

Referring again to FIG. 8, the operation of the second embodiment is described below.

As illustrated in FIG. 8, when the operator instructs the calibration of the visual axis of the right eye through the operation of the keyboard or mouse, the MPU 31 of the operator unit 12 displays the gaze image GT to be gazed at by the test subject using the right eye, in the right eye image display area of the display screen of the display for test subjects, as illustrated in FIG. 7A, through the multimedia interface 35 (Step S41).

At this time, the operator prompts the test subject to gaze at the gaze image GT, in order to restrict changes in the position of the visual axis (line of vision) of the subject.

Accordingly, the MPU 31 of the operator unit 12 calculates the optical axis of the right eye, with the changes in the visual axis of the right eye being restricted (Step S42).

An optical axis calculation processing in the second embodiment is described below in detail.

Figure 21:
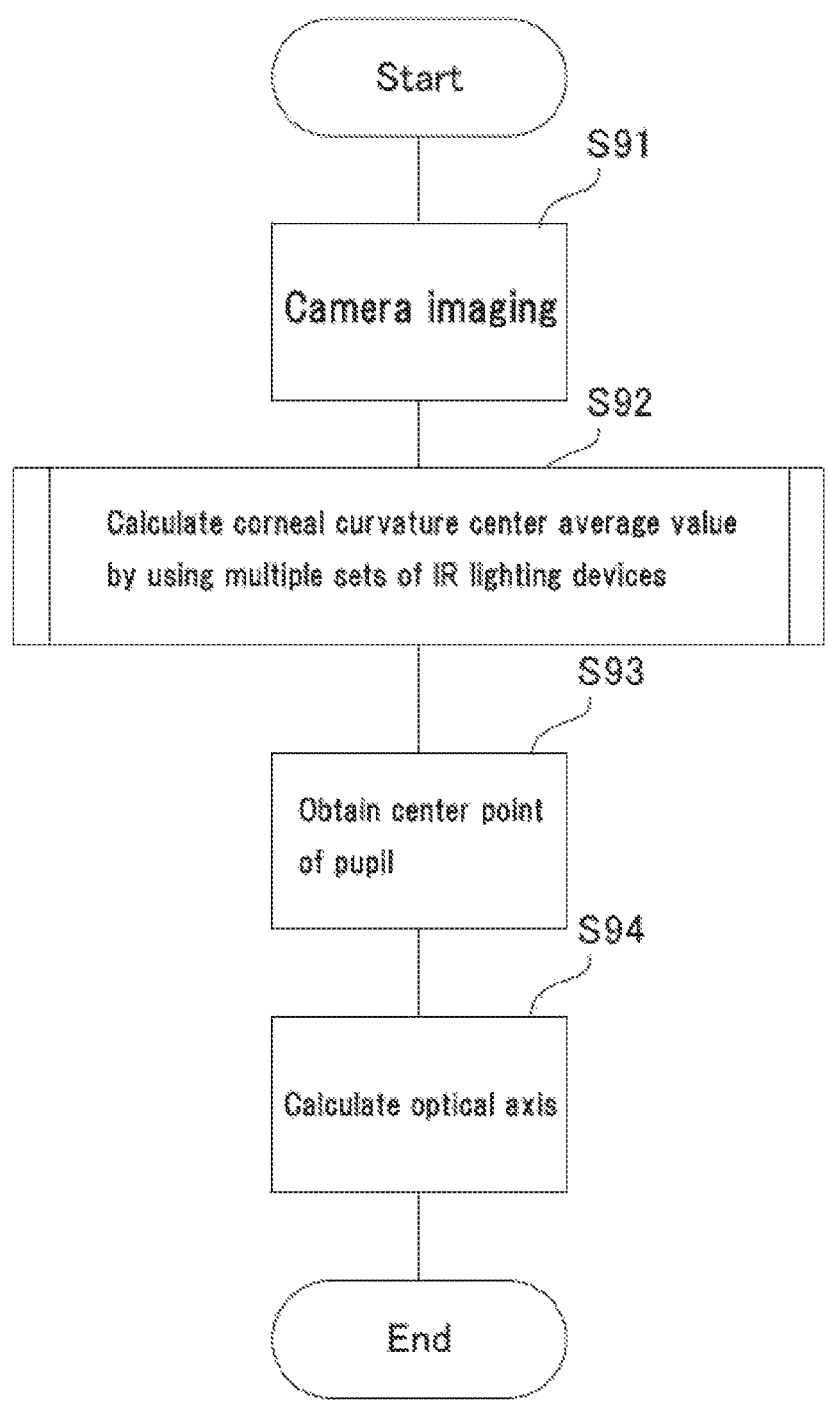
FIG. 21 is a processing flowchart of an optical axis calculation according to the second embodiment.

FIG. 21 is a processing flowchart of an optical axis calculation according to the second embodiment.

Initially, the MPU 31 of the operator unit 12 controls the IR lighting devices LED11 to LED18 through the control interface 36 and the control interface 28, and causes each of the IR lighting devices to emit the test light L, and further controls the eyeball cameras 23R and 23L to image the eyeballs (Step S91).

Subsequently, the MPU 31 calculates a corneal curvature center average value by using multiple sets of IR lighting devices (Step S92).

A method for calculating a corneal curvature center average value (a representative value of the corneal curvature centers) is described below in detail.

Figure 22:
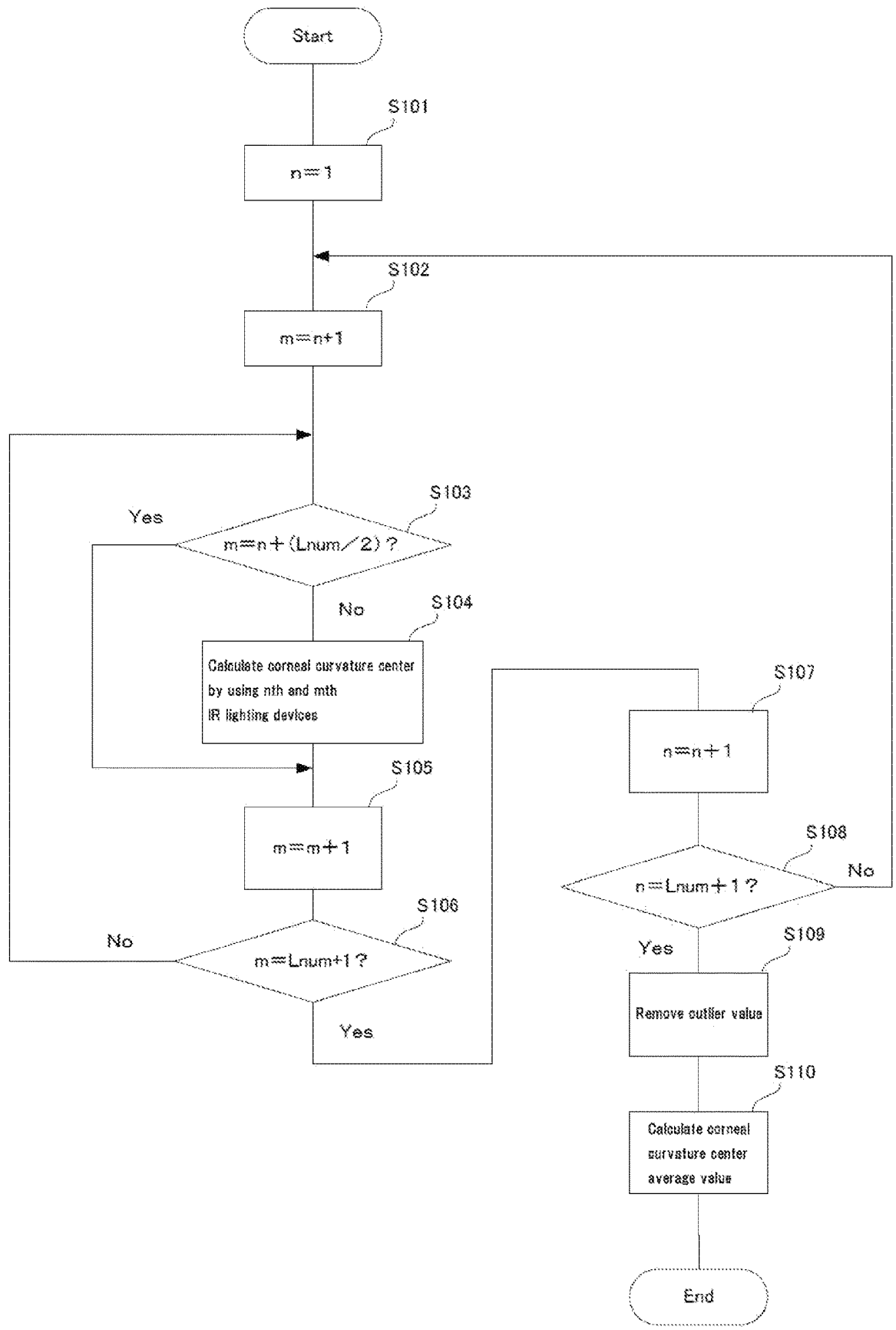
FIG. 22 is a processing flowchart of calculating a corneal curvature center average value according to the second embodiment.

FIG. 22 is a processing flowchart of calculation processing of a corneal curvature center average value according to the second embodiment.

Initially, the MPU 31 of the operator unit 12 sets a parameter n for specifying a first IR lighting device to 1, which is an initial value (Step S101). In this case, the value of the parameter n corresponds to any of the IR lighting devices. In the example in FIG. 21, for example, n=1 represents the IR lighting device LED11, and n=2 represents the IR lighting device LED12, . . . , and n=8=nmax represents the IR lighting device LED18.

Then, the MPU 31 sets a parameter m for specifying a second IR lighting device to n+1, which is an initial value (Step S102). In this case, the value of the parameter m also corresponds to any of the IR lighting devices. In the example in FIG. 21, for example, if n=1, then m=2, and the IR lighting device LED12 is represented, and if n=2, then m=3, and the IR lighting device LED13 is represented, . . . , and if n=7, then m=8, and the IR lighting device LED18 is represented. Note that if n=8, then m=9, but the IR lighting device LED11, which is located next to the IR lighting device LED18, is represented.

Then, if the first IR lighting device and the second IR lighting device meet a condition that disables measurement, then the MPU 31 determines to exclude these devices from the optical axis calculation (Step S103).

More specifically, this is because, when the first IR lighting device and the second IR lighting device are located at 180° with respect to each other, a first plane that includes the position of the first IR lighting device, the reflection image position, and the optical center of the camera, and a second plane that includes the position of the second IR lighting device, the reflection image position, and the optical center of the camera are theoretically equal, and thus the intersection line of the two planes cannot be specified, and it is impossible to identify where the corneal curvature center is located.

In addition, when the first IR lighting device and the second IR lighting device are located at 180° with respect to each other, the equation below is satisfied, and in this case, these devices are excluded from the optical axis calculation:

$$m=n+(Lnum/2)$$

In this equation, Lnum is the number of IR lighting devices. In the example of FIG. 22, Lnum=8.

More specifically, in the second embodiment, an even number of IR lighting devices are provided and spaced apart from one another at an equal angle. Therefore, if a current parameter m is a value obtained by adding a value of ½ of the number Lnum of the IR lighting devices, this means that the first IR lighting device corresponding to the parameter n and the second IR lighting device corresponding to the parameter m=n+(Lnum/2) are located at 180° with respect to each other. Therefore, these devices are excluded from the optical axis calculation.

Still more specifically, in the example described above, a combination of n=1 and m=5, a combination of n=2 and m=6, a combination of n=3 and m=7, and a combination of n=4 and m=8 are to be excluded from the optical axis calculation.

In addition, even when the first IR lighting device and the second IR lighting device are not located at 180° with respect to each other, as long as the first IR lighting device and the second IR lighting device are located at a position close to 180° (within ±α° range), for example at a position within a range of 180±10°, it is possible to configure so that the devices in such conditions are also excluded.

Following the processing described above, the MPU 31 of the operator unit 12 calculates the corneal curvature center by using an $n^{th}$ IR lighting device LEDn and an $m^{th}$ IR lighting device LEDm, as described later (Step S104).

The calculation of the corneal curvature center, and the calculation of an optical axis based on the calculated corneal curvature center are described below in detail.

Figure 23:
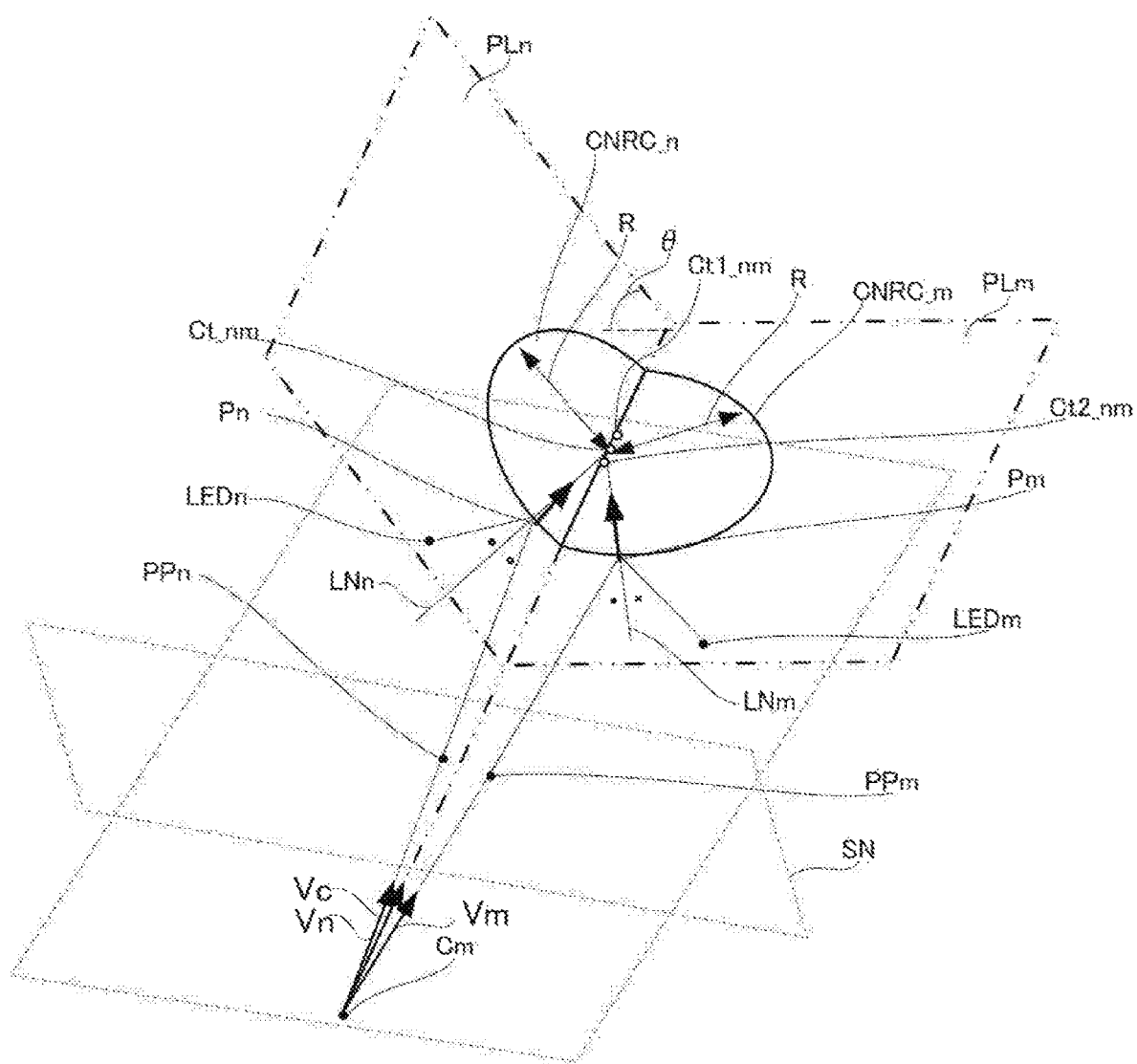
FIG. 23 is a diagram illustrating a principle of a method for calculating the corneal curvature center and the optical axis of the second embodiment.

FIG. 23 is a diagram illustrating a principle of a method for calculating the corneal curvature center and the optical axis of the second embodiment.

In FIG. 23, a corneal curvature ball CNRC having a curvature equal to the cornea is assumed, and its corneal curvature center is defined as Ct, and the radius of the corneal curvature ball CNRC is defined as R, and the optical center of a camera is defined as Cm.

The $n^{th}$ IR lighting device LEDn (any one of n=1 to 8 in the second embodiment) and the $m^{th}$ IR lighting device LEDm (m=1 to 8 (where m≠n), in the second embodiment) are both regarded as point light sources.

In addition, the reflection image position of the IR lighting device LEDn in a three dimensional space is defined as Pn, and the reflection image position of the IR lighting device LEDm in a three dimensional space is defined as Pm.

At this time, when a plane that includes the position LEDn of the IR lighting device LEDn, the reflection image position Pn, and the optical center Cm of the camera is defined as PLn, and a plane that includes the position LEDm of the IR lighting device LEDm, the reflection image position Pm, and the optical center Cm of the camera is defined as PLm, then an intersection line CLnm of the plane PLn and the plane PLm passes through the corneal curvature center Ct.

Therefore, the unit vector from the optical center Cm of the camera toward the corneal curvature center Ctnm of the cornea on the intersection line CLnm is defined as Vc, and the unit vector from the optical center Cm of the camera toward the reflection image position Pn on the plane PLn is defined as Vn, and the unit vector from the optical center Cm of the camera toward the reflection image position Pm on the plane PLm is defined as Vm.

In addition, the vector from the reflection image position Pn toward the corneal curvature center Ctnm on the plane PLn is defined as f, and the vector from the reflection image position P2 toward the corneal curvature center Ct on the plane PL2 is defined as g.

From the conditions described above, the following is satisfied.

(1) The corneal curvature center Ct is located at a position where the unit vector Vc is multiplied by the constant t0 (t0 is a positive real number). Therefore, in the description below, the corneal curvature center at a stage where the constant t0 is unknown is defined as a first assumed corneal curvature center Ct1_nm.

(2) The reflection image position Pn is located at a position where the unit vector Vn is multiplied by the constant t1 (t1 is a positive real number). In the second embodiment, n=any of 1 to 8.

(3) The reflection image position Pm is located at a position where the unit vector Vm is multiplied by the constant t2 (t2 is a positive real number). In the second embodiment, m=1 to 8, and m≠n.)

(4) The reflection image position Pn and the reflection image position Pm are located at a distance of the radius of the corneal curvature R from the corneal curvature center Ctnm.

The MPU 31 of the operator unit 12 sets the radius R of the corneal curvature ball CNRC to a predetermined value, based on the image captured in Step S91, and then calculates the reflection image position P1 and the reflection image position P2.

Then, the MPU 31 of the operator unit 12 calculates the plane PLn that includes the position LEDn of the IR lighting device LEDn, the reflection image position Pn, and the optical center Cm of the camera, each corresponding to the current value of n. The MPU 31 further calculates a plane PLm that includes the position LEDm of the IR lighting device LEDm, the reflection image position Pm, and the optical center Cm of the camera, each corresponding to the current value of m.

Subsequently, the MPU 31 of the operator unit 12 calculates an intersection line of the two planes PLn and PLm, from the plane PLn (equation that expresses the plane PLn) and the plane PLm (equation that expresses the plane PLm).

In addition, the MPU 31 of the operator unit 12 calculates the unit vector Vn from the reflection image position Pn described above, and then obtains the vector f from the calculated unit vector Vn, and the reflection image position Pn and the position LED1 of the IR lighting device LEDn.

In addition, the MPU 31 of the operator unit 12 calculates the unit vector Vm from the reflection image position Pm described above, and then obtains the vector g from the calculated unit vector Vm, and the reflection image position Pm and the position LEDm of the IR lighting device LEDm.

Then, the MPU 31 of the operator unit 12 estimates the position of the corneal curvature center Ct_nm, and calculates the constant to.

Initially, the MPU 31 of the operator unit 12 assumes a first straight line LNn along the orientation of the vector f from the reflection image position Pn, and assumes a second straight line LNm along the orientation of the vector g from the reflection image position Pm. The MPU 31 then calculates an intersection point of the straight line LNn and the straight line LNm (or the closest point from both of the two straight lines (nearest neighbor point)), and defines it as a second estimated corneal curvature center Ct2_nm.

In this case, the first estimated corneal curvature center Ct1_nm and the second estimated corneal curvature center Ct2_nm should actually be equal, and thus the constant t0 may be calculated such that the equation below is minimized.

$$|Ct1\_nm - Ct2\_nm|$$

Hereinafter, the constant t0 is calculated in conformity to the principle described above.

Initially, the MPU 31 of the operator unit 12 calculates the unit vector Vc, based on the intersection line of the two planes PLn and PLm.

More specifically, if a vector Vc1 that is in the same orientation as the unit vector Vc is assumed, then the equation below is satisfied.

$$Vc1 = \{(LEDn - Cm) \times (PPn - Cm)\} \times \{(LEDm - Cm) \times (PPm - Cm)\}$$

In this equation, PPn is the position on an imaging sensor of the camera at the reflection image position Pn, and PPm is the position on the imaging sensor of the camera at the reflection image position Pm.

The unit vector Vc can be expressed by the equation below.

$$Vc = Vc1/\|Vc1\|$$

In this equation, $\|Vc1\|$ is the magnitude (scalar) of the vector Vc1.

Then, the MPU 31 of the operator unit 12 calculates the unit vector Vn and the unit vector Vm, from the optical center Cm of the camera, the position PPn, and the position PPm.

$$Vn = (Cm - PPn)/\|Cm - PPn\|$$

$$Vm = (Cm - PPm)/\|Cm - PPm\|$$

The first assumed corneal curvature center Ct1_nm that corresponds to the corneal curvature center Ct_nm should be placed at a position where the unit vector Vc is multiplied by the constant t0, when the optical center Cm of the camera is used as a base point. Therefore, the following equation is satisfied.

$$Ct1\_nm = t0 \cdot Vc + Cm$$

In addition, the reflection image position Pn and the reflection image position Pm are calculated on the assumption that: the reflection image position Pn is located at a position where the unit vector Vn is multiplied by the constant t1, using the optical center Cm of the camera as a base point; and the reflection image position Pm is located at a position where the unit vector Vm is multiplied by the constant t2 from the optical center Cm of the camera as a base point; and the reflection image position Pn and the reflection image position Pm are located at a position of the corneal curvature radius R from the corneal curvature center Ct_nm.

More specifically, as follows:
when Pn = t1·Vn + Cm, then $$R^2 = \|t0 \cdot Vc\|^2 + \|t1 \cdot Vn\|^2 - 2 \cdot t0 \cdot t1 \cdot Vc \cdot Vn,$$

which results in:

$$t1 = t0 \cdot Vc \cdot Vn \pm \sqrt{\{(\|Vc \cdot Vn\|^2 - 1) \cdot t0^2 + R^2\}}.$$

In the equation, the positive sign (+) in the double sign (±) corresponds to the intersection point located backward as viewed from the camera, among two intersection points at which the sphere having the radius R centering at the corneal curvature center Ct_nm intersect a straight line passing through the optical center Cm of the camera and the reflection image position Pn. Therefore, the negative sign (−) that corresponds to the intersection point located forward as viewed from the camera is the constant t1 to be obtained.

Similarly, if Pm=t2·Vm+Cm, then $$R^2 = \|t0 \cdot Vc\|^2 + \|t2 \cdot v2\|^2 - 2 \cdot t0 \cdot t2 Vc \cdot Vm,$$

which results in:

$$t2 = t0 \cdot Vc \cdot v2 \pm \sqrt{\{(\|Vc \cdot Vm\|^2 - 1) \cdot t0^2 + R^2\}}.$$

Also in this case, the positive sign (+) in the double sign (±) corresponds to the intersection point located backward as viewed from the camera, among the two intersection points at which the sphere having the radius R centering at the corneal curvature center Ct_nm intersect a straight line passing through the optical center Cm and the reflection image position Pm of the camera. Therefore, the negative sign (−) that corresponds to the intersection point located forward as viewed from the camera is the constant t2 to be obtained.

Subsequently, the vector f and vector g are obtained as described below.

Following equations can be obtained from the relationship between the unit vector Vn, and the reflection image position Pn and the $n^{th}$ IR lighting device LEDn, and the relationship between the unit vector Vm, and the reflection image position Pm and the $m^{th}$ IR lighting device LEDm.

$$f = Vn + (Pn - LEDn)/\|Pn - LEDn\|$$

$$g = Vm + (Pm - LEDm)/\|Pm - LEDm\|$$

Then, the MPU 31 of the operator unit 12 assumes a first straight line LNn passing through the reflection image position Pn and along the orientation of the vector f, and assumes a second straight line LNm passing through the reflection image position Pm and along the orientation of the vector g, and calculates the intersection point of the straight line LNn and the straight line LNm (or the nearest point from both of the two straight lines (nearest neighbor point) is calculated) as the second estimated corneal curvature center Ct2_nm.

$$Ct2\_nm = \frac{1}{2}[f \cdot g]\begin{bmatrix} \|f \cdot f\| & -\|f \cdot g\| \\ -\|f \cdot g\| & \|g \cdot g\| \end{bmatrix}^{-1}\begin{bmatrix} -f \cdot (Pn - Pm) \\ g \cdot (Pn - Pm)) \end{bmatrix} + \frac{1}{2}(Pn + Pm) \quad \text{[Equation 3]}$$

In this case, the first estimated corneal curvature center Ct1_nm and the second estimated corneal curvature center Ct2_nm should be equal to the corneal curvature center Ct_nm, respectively. Therefore, the constant t0 that minimizes an evaluation value X is calculated, which is a difference between the first estimated corneal curvature center Ct1_nm and the second estimated corneal curvature center Ct2_nm.

In other words, the constant t0 that satisfies the equation below is calculated.

$$X = \arg_{t0}^{min} \|Ct1\_nm - Ct2\_nm\|^2 \quad \text{[Equation 4]}$$

Then, processing is described referring again to FIG. 22.

After the calculation of the corneal curvature center using the $n^{th}$ and $m^{th}$ IR lighting devices is completed (Step S104), the MPU 31 adds 1 to the value of m (Step S105). In other words, m=m+1.

Subsequently, the MPU 31 determines whether or not the value of m is equal to a value obtained by adding 1 to the number Lnum of the IR lighting devices, i.e., m=Lnum+1 (Step S106).

In the determination in Step S106, if it is determined that m<Lnum+1 ("No" in Step S106), then the MPU 31 returns the processing back to Step S103, and repeats the processing described above. In other words, for all corresponding values of the parameter m, the optical axis and the corneal curvature center are calculated for the value of one parameter n.

In the determination in Step S106, if it is determined that m=Lnum+1 ("Yes" in Step S106), this means that the processing for the value of the parameter n is completed, and thus the MPU 31 adds 1 to the value of n, in order to set the value of the parameter n to a new value (Step S107). In other words, it results in n=n+1.

Subsequently, the MPU 31 determines whether or not the value of n is equal to a value obtained by adding 1 to the number Lnum of the IR lighting devices, i.e. n=Lnum+1 (Step S108).

In the determination in Step S108, if it is determined that n<Lnum+1 ("No" in Step S108), then the MPU 31 returns the processing back again to Step S93, and repeats the processing described above. In other words, for the value of new parameter n, the optical axis and the corneal curvature center are calculated for all corresponding values of the parameter m.

In the determination in Step S108, if it is determined that n=Lnum+1 ("Yes" in step S108), which means that the processing for all combinations of the parameter n and parameter m for performing optical axis calculation (in the case of the example described above, all twenty four combinations, i.e., the combinations $_8C_2$ selecting two different IR lighting devices out of the eight IR lighting devices, minus four combinations being located at 180° with respect to each other) is completed, then the MPU 31 performs a processing to remove an outlier value (Step S109).

As a method for removing an outlier value, for example, a value near the maximum value and the minimum value of data, out of the twenty four calculated corneal curvature center values, can be excluded from the calculation of the average value (so-called trim averaging).

Subsequently, the MPU 31 calculates a corneal curvature center average value after removing the outlier value from the corneal curvature centers calculated in Step S104 (the average value of corneal curvature center in a three dimensional space), as a corneal curvature center average value (Step S110).

After the corneal curvature center average value is calculated, the MPU 31 of the operator unit 12 obtains the center point of the pupil, based on the captured image of the eyeball camera 23R (Step S93).

Then, the MPU 31 connects the calculated center point of the pupil, and the corneal curvature center Ct calculated by the constant t0 and the unit vector v0, and calculates as an optical axis of the eye (Step S94).

Referring again to FIG. 8, the processing of the optical axis calculation is described.

Then, the MPU 31 calculates a difference between the optical axis calculated in Step S56 and the visual axis, as the correction amount (optical axis correction amount) (step S43).

More specifically, the MPU 31 calculates a difference between the optical axis calculated in Step S94 and the visual axis (line of vision) of the test subject as a correction amount (optical axis correction amount), such that the calculated optical axis coincides with the visual axis (line of vision) of the test subject, in other words, such that the display position of the visual axis mark image GVA (which corresponds to the position of the optical axis passing through the calculated the corneal curvature center average value) coincides with the gaze image GT (which corresponds to the visual axis (line of vision) position of the test subject).

The MPU 31 corrects the calculated optical axis by the correction amount obtained in Step S43, and estimates the visual axis of the subject as needed (Step S44).

As described above, according to the second embodiment, the accuracy of the optical axis estimation can be improved, adding to the effects of the first embodiment, and thus a test with high accuracy can be done.

[2.1] First Modification Example of the Second Embodiment

Figure 24:
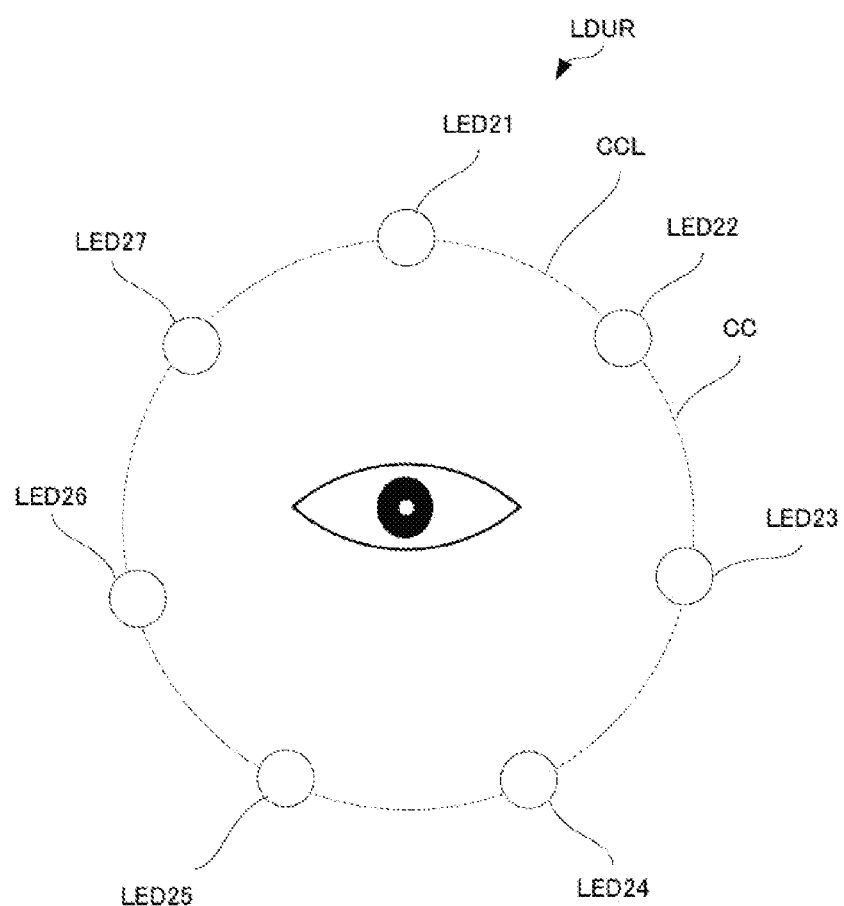
FIG. 24 is a diagram illustrating arrangement positions of LEDs in an LED unit in a modification example of the second embodiment.

FIG. 24 is a diagram illustrating arrangement positions of LEDs in an LED unit of a first modification example of the second embodiment.

The present modification example differs from the second embodiment in that an odd number of IR lighting devices are disposed on the circumference of a circle CCL at the same angle apart, on a plane that intersects a visual axis of a test subject (an axis that intersects the page of the drawing).

In the example illustrated in FIG. 24, seven IR lighting devices LED21 to LED27 are disposed on the circumference of a circle CCL on a plane that intersects a visual axis of a test subject (an axis that intersects the page), at the same angle apart (at 360°/7=approximately 51.4° apart), and thus no IR lighting device is located at the position that meets a condition that disables measurement, i.e., 180° with respect to any other IR lighting device.

Therefore, the optical axis position can be calculated even when any two of the IR lighting devices are selected. In this case, the processing in Step S103 in FIG. 22 can be omitted so that processing can be performed at a higher speed.

Also in this modification example, similarly to the second embodiment, even when the first IR lighting system and the second IR lighting system are not located at 180° with respect each other, if they are located at an angle close to 180° (within ±α° range: a condition that reduces measurement accuracy), for example, when they are disposed at within a range of 180±10°, the measurement accuracy of the optical axis is reduced. Therefore, it is possible to configure these devices in such conditions are also to be excluded.

More specifically, when the first IR lighting device and the second IR lighting device are disposed at a position in the range of 180±10°, it is possible to specify a first plane that includes the position of the first IR lighting device, the reflection image position, and the optical center of the camera, and a second plane that includes the position of the second IR lighting device, the reflection image position, and the optical center of the camera. However, in this case, the accuracy in specifying an intersection line of the two planes decreases, and the accuracy of the measurement of the corneal curvature center decreases, and thus the accuracy of the measurement of the optical axis decreases. Therefore, it is possible to configure so that the devices are to be excluded also in these conditions.

[2.2] Second Modification Example of the Second Embodiment

In the second embodiment and the first modification example of the second embodiment, multiple IR lighting devices are disposed at the same angle apart on the circumference of the circle on the plane that intersects the visual axis of the subject. However, it is also possible to dispose multiple IR lighting devices at an arbitrary angle on the circumference of a circle on a plane that intersects the visual axis of the subject, when the condition that disables measurement or measurement accuracy is satisfied.

[2.3] Third Modification Example of the Second Embodiment

In the description above, the IR lighting devices LED11 to LED18 are disposed on the circumference of the circle on the plane that intersects the visual axis of the test subject (the axis that intersects the page on the drawing). However, if three or more IR lighting devices are used and three dimensional arrangement positions of each device with reference to the optical center position of the camera are known, then a plane that includes the position of the IR lighting device, the reflection image position, and the optical center of the camera can be easily specified.

Therefore, among the three or more IR lighting devices, any of the IR lighting devices does need not to be coplanar with other IR lighting devices (i.e., the devices may be located on multiple planes that intersect the visual axis of the test subject.

In addition, among the three or more IR lighting devices, any of the IR lighting devices does need to be on the same circumference, when an orthographic projection of each IR lighting device is projected onto one plane that intersects the visual axis of the subject, or onto the same plane orthogonal to the visual axis when three or more IR lighting devices are disposed on multiple planes that intersect the visual axis of the test subject.

In addition, when an orthographic projection of each IR lighting device is projected onto the same plane orthogonal to the visual axis, it is not necessary to dispose the IR lighting devices at the same angle apart on the plane that intersects the visual axis.

However, in terms of ensuring measurement accuracy, it is preferable to dispose IR lighting devices at dispersed positions to surround a visual axis, when an orthographic projection of each IR lighting device is projected on the same plane orthogonal to the visual axis. For example, when four IR lighting devices are disposed, it is preferable that one IR lighting device is disposed in each of first to four quadrants on a coordinate plane formed by an X-axis and a Y-axis that are orthogonal to each other, using the visual axis as the origin point, on the plane orthogonal to the visual axis.

[3] Third Embodiment

In the description above, the visual function test device is described as an example of the first embodiment or the second embodiment. However, the description can be similarly applied to a visual function training device for performing a visual function training using a display on a test subject display screen.

More specifically, it is possible for a trainee to easily recognize which position is actually used as a gaze position in a visual function training and obtain a greater visual function training effect, also in a fusion training device for training fusion ability to fuse images of the right and left retinas into a single vision (fused into a single image), used for a patient (trainee) who suffers diplopia in both eyes in which an object is seen as two objects. Another example of the visual function training device may be a stereopsis training device or the like that performs a stereopsis vision training (near vision training (so-called crossing method) and far vision training (so-called parallel method)) for improving an ability of an eye by performing stereopsis vision.

In this case, the examiner (operator) in the description above may be replaced with a trainer, the test subject may be replaced with a trainee, and the test subject display may be replaced with a trainee display, and the test processing may be replaced with a training processing, as appropriate.

[4] Modification Example of Embodiments

In the description above, a nine gaze directions test has been explained as the visual function test. However, embodiments are applicable also to a visual acuity test (a test with a single eye opened and a test with both eyes opened), a simultaneous perception test, a fusion test, a stereopsis test (near vision test and far vision test), a visual field test, a preferred gaze (Preferential looking method) test, an aniseikonia test, etc.

In the description above, a chart having a square shape (like graph paper) is used as a chart for the nine gaze directions test. However, it is also possible to use a curved nine gaze directions test for projection, which is conventionally well known.

Although several embodiments of the invention have been described above, these embodiments are merely for illustration and are not intended to limit the scope of the invention. These embodiments may be implemented in various other aspects, and various omissions, substitutions, or changes may be made without departing from the spirit of the invention. These embodiments and their modifications are included within the range and spirit of the invention, and included in the invention described in claims, and the range of their equivalents.

10,10A Visual function test device
11 Test unit
12 Operator unit
13 Test table
14 Jaw table
21 Optical system unit
21L Optical system unit
21R Optical system unit
21L Eyeball camera
23R Eyeball camera
24 Test subject display
24D Display screen
25 Multimedia interface
26 Audio/video separation portion
27 Loudspeaker portion
28 Control interface
31 MPU
32 ROM
33 RAM
34 Flash memory
35 Multimedia interface
36 Control interface
37 Operator display
37D Display screen
38 Printer
39 Mouse
40 Keyboard
41 External storage medium connector portion
LD1, LD2 IR lighting device
LDUR, LDUL IR lighting unit device
LED11-LED18, LED21-LED27 IR lighting device
MML1 Gaze position image
MML2 Gaze position image
MMR1 Gaze position image
MMR2 Gaze position image
MP1-MP9 Measurement point

The invention claimed is:

1. A visual function test device comprising:
   a display device for a test subject;
   a display device for an operator;
   a target display portion for displaying a target image to be viewed by the test subject, onto the display device for the test subject;
   a visual axis estimation portion for estimating a visual axis of the test subject when the target image is viewed by the test subject;
   a position display portion for displaying a display position of the target image and a viewpoint position that corresponds to the estimated visual axis, onto the display device for the operator; and
   a display portion for displaying an eyeball image of the test subject, onto the display device for the operator.

2. The visual function test device according to claim 1, wherein the visual axis estimation portion calculates an optical axis correction amount, based on an optical axis calculated from a spatial coordinate of the target image and a spatial coordinate of a corneal curvature center assuming a cornea of the test subject and based on a visual axis of the test subject specified at a time of the calculation of the optical axis, and corrects the optical axis of the test subject when a desired one of the target image is viewed by the test subject using the optical axis correction amount, and estimates the optical axis.

3. The visual function test device according to claim 2, wherein the visual axis estimation portion:
   calculates the optical axis correction amount per eye in a calibration prior to an actual test, and
   uses the optical axis correction amount in correcting all corrections of the optical axis performed in the actual test.

4. The visual function test device according to claim 1, wherein the target image is used as an image that represents a position corresponding to any of a plurality of measurement points in a nine gaze directions test.

5. The visual function test device according to claim 4, comprising:
   a test result display portion for storing viewpoint positions that correspond to the plurality of measurement points, and displaying the plurality of viewpoint positions in an image as a test result image onto a nine gaze directions test chart image after the nine gaze directions test is completed, wherein the plurality of viewpoint positions are connected in a predefined correspondence relationship in the image.

6. The visual function test device according to claim 4, wherein the test result display portion superimposes and displays a test result image of a right eye and a test result image of a left eye on the nine gaze directions test chart image as the test result image.

7. The visual function test device according to claim 1, comprising:
   a plurality of IR lighting devices each for illuminating an eyeball of the test subject using test light; and
   an imaging device for imaging a reflected image of the test light reflected from the eyeball,
   wherein the visual axis estimation portion estimates the visual axis, based on respective positions of a pair of IR lighting devices of a selected one set or multiple sets of IR lighting devices among the plurality of IR lighting devices, a respective position of the reflected image, and an optical center of the imaging device.

8. The visual function test device according to claim 7, wherein the plurality of the IR lighting devices are disposed on one or more planes intersecting a visual axis of the test subject.

9. The visual function test device according to claim 8, wherein the IR lighting devices are disposed on the circumference of a circle on one plane intersecting a visual axis of the test subject, at every predefined cycle.

10. The visual function test device according to claim 9, wherein, when a set of the IR lighting devices is to be selected among the IR lighting devices, the visual axis estimation portion excludes any set of IR lighting device that meets a condition that disables measurement or a condition that reduces measurement accuracy, with respect to one of the IR lighting devices.

11. The visual function test device according to claim 8, wherein the plurality of IR lighting devices are disposed to surround the visual axis of the test subject.

12. The visual function test device according to claim 7, wherein the plurality of IR lighting devices are disposed at positions whose three dimensional position with respect to an optical center position of a camera are respectively known.

13. The visual function test device according to claim 12, wherein the plurality of IR lighting devices are disposed to surround the visual axis of the test subject.

14. A visual function training device comprising:
a display device for a trainee;
a display device for an operator;
a target display portion for displaying a target image to be viewed by the trainee onto the display device for the trainee;
a visual axis estimation portion for estimating a visual axis of the trainee when the target image is viewed by the trainee;
a position display portion for displaying a display position of the target image and a viewpoint position that corresponds to the estimated visual axis, onto the display device for the operator; and
a display portion for displaying an eyeball image of the trainee onto the display device for the operator.

15. The visual function training device according to claim 14,
wherein the visual axis estimation portion calculates an optical axis correction amount, based on an optical axis calculated from a spatial coordinate of the target image and a spatial coordinate of a corneal curvature center assuming a cornea of the trainee and based on a visual axis of the trainee specified at a time of the calculation of the optical axis, and corrects the optical axis of the trainee when a desired one of the target image is viewed by the trainee using the optical axis correction amount, and estimates the optical axis.

16. The visual function training device according to claim 15, wherein the visual axis estimation portion:
calculates the optical axis correction amount per eye in a calibration prior to an actual training, and
uses the optical axis correction amount in correcting all corrections of the optical axis used for the actual training.

17. A method performed in a visual function test device equipped with a display device for a test subject and a display device for an operator, the method comprising a step of:
displaying a target image to be viewed by the test subject onto the display device for the test subject;
estimating a visual axis of the test subject when the target image is viewed by the test subject;
displaying a display position of the target image and a viewpoint position that corresponds to the estimated visual axis, onto the display device for the operator; and
displaying an eyeball image of the test subject onto the display device for the operator.

18. The method according to claim 17,
wherein the visual function test device comprises: a plurality of IR lighting devices each for illuminating an eyeball of the test subject using test light; and an imaging device for imaging a reflected image of the test light from the eyeball,
wherein the step of estimating the visual axis estimates the visual axis, based on respective positions of a pair of the IR lighting devices of a selected one set or multiple sets of the plurality of IR lighting devices, a respective position of the reflected image, and an optical center of the imaging device.

19. The method described in claim 17:
wherein the test subject is a trainee; and
the method comprising a step of displaying the target image to be viewed by the trainee onto the display device for the test subject, thereby visual function training can be performed.

20. The method according to claim 19,
wherein the visual function test device comprises: a plurality of IR lighting devices each for illuminating an eyeball of the trainee using test light; and an imaging device for imaging a reflected image of the test light from the eyeball,
wherein the step of estimating the visual axis estimates the visual axis, based on respective positions of a pair of the IR lighting devices of a selected one set or multiple sets of the plurality of IR lighting devices, a respective position of the reflected image, and an optical center of the imaging device.

* * * * *